(12) United States Patent
Kadziauskas et al.

(10) Patent No.: US 7,938,120 B2
(45) Date of Patent: *May 10, 2011

(54) ENHANCED MICROBURST ULTRASONIC POWER DELIVERY SYSTEM AND METHOD

(75) Inventors: Kenneth E. Kadziauskas, Coto de Caza, CA (US); Paul W. Rockley, Corona del Mar, CA (US)

(73) Assignee: Abbott Medical Optics, Inc., Santa Ana, CA (US)

( * ) Notice: Subject to any disclaimer, the term of this patent is extended or adjusted under 35 U.S.C. 154(b) by 697 days.

This patent is subject to a terminal disclaimer.

(21) Appl. No.: 11/415,730

(22) Filed: May 1, 2006

(65) Prior Publication Data

US 2006/0200068 A1 Sep. 7, 2006

Related U.S. Application Data

(63) Continuation of application No. 10/278,775, filed on Oct. 21, 2002, now Pat. No. 7,077,820.

(51) Int. Cl.
*A61B 19/00* (2006.01)
(52) U.S. Cl. ............. 128/698; 606/169; 604/19; 604/22
(58) Field of Classification Search .................. 128/898; 606/4–6, 10–12, 167, 169–171; 604/19, 604/21, 22, 28, 44; 600/437, 439, 446, 452; 601/2

See application file for complete search history.

(56) References Cited

U.S. PATENT DOCUMENTS

| | | | |
|---|---|---|---|
| 2,434,480 A | 1/1948 | Anderson | |
| 3,857,387 A | 12/1974 | Shock | |
| 3,941,122 A | 3/1976 | Jones | |
| 4,184,510 A | 1/1980 | Murrey et al. | |
| 4,343,111 A | 8/1982 | Inoue | |
| 4,736,130 A | 4/1988 | Puskas | |
| 4,808,948 A | 2/1989 | Patel et al. | |
| 4,827,911 A | 5/1989 | Broadwin et al. | |
| 4,952,834 A | 8/1990 | Okada | |
| 4,954,960 A | 9/1990 | Lo et al. | |
| 4,970,656 A | 11/1990 | Lo et al. | |
| 4,983,901 A | 1/1991 | Lehmer | |

(Continued)

FOREIGN PATENT DOCUMENTS

DE 19940712 8/1999

(Continued)

OTHER PUBLICATIONS

Devine, M.D. et al. "How to set the dials, Phacoemulsification Surgery", 1991, pp. 7-28, Pergamon Press, NY.

(Continued)

*Primary Examiner* — Ahmed M Farah
(74) *Attorney, Agent, or Firm* — Smyrski Law Group, A P.C.

(57) ABSTRACT

A method and apparatus for delivering energy during a surgical procedure such as phacoemulsification is provided. The method and apparatus include applying energy during at least one pulsed energy on period, comprising applying energy during a series of short burst periods, the short burst periods interspersed by short rest periods. The method and apparatus further comprise delivering minimal energy during a long off period, the long off period comprising a relatively long period when minimal energy is applied, wherein one long off period follows each pulsed energy on period. The short burst periods and the short rest periods are relatively brief in duration as compared with the long off period.

30 Claims, 20 Drawing Sheets

U.S. PATENT DOCUMENTS

| | | | |
|---|---|---|---|
| 5,001,649 A | 3/1991 | Lo et al. |
| 5,091,656 A | 2/1992 | Gahn |
| 5,209,221 A | 5/1993 | Riedlinger |
| 5,213,569 A | 5/1993 | Davis |
| 5,242,404 A | 9/1993 | Conley et al. |
| 5,249,121 A | 9/1993 | Baum et al. |
| 5,268,624 A | 12/1993 | Zanger |
| 5,279,547 A | 1/1994 | Costin |
| 5,318,563 A | 6/1994 | Malis et al. |
| 5,331,951 A | 7/1994 | Kepley |
| 5,342,293 A | 8/1994 | Zanger |
| 5,370,602 A | 12/1994 | Kepley |
| 5,388,569 A | 2/1995 | Kepley |
| 5,403,307 A | 4/1995 | Zelman |
| 5,405,614 A | 4/1995 | D'Angelo et al. |
| 5,406,503 A | 4/1995 | Williams, Jr. et al. |
| 5,417,246 A | 5/1995 | Perkins et al. |
| 5,431,664 A | 7/1995 | Ureche et al. |
| 5,453,087 A | 9/1995 | Malinowski |
| 5,520,633 A | 5/1996 | Costin |
| 5,534,741 A | 7/1996 | Smith |
| 5,547,459 A | 8/1996 | Kaufman et al. |
| 5,582,578 A | 12/1996 | Zhong et al. |
| 5,591,127 A | 1/1997 | Barwick et al. |
| 5,700,240 A | 12/1997 | Barwick et al. |
| 5,733,256 A | 3/1998 | Costin et al. |
| 5,738,677 A | 4/1998 | Colvard et al. |
| 5,766,146 A | 6/1998 | Barwick, Jr. |
| 5,797,494 A | 8/1998 | Balling et al. |
| 5,800,365 A | 9/1998 | Zhong et al. |
| 5,808,396 A | 9/1998 | Boukhny |
| 5,836,959 A | 11/1998 | Seibel et al. |
| 5,852,794 A | 12/1998 | Staggs |
| 5,873,885 A | 2/1999 | Weidenbenner |
| 5,938,677 A | 8/1999 | Boukhny et al. |
| 5,979,494 A | 11/1999 | Perkins et al. |
| 5,984,882 A | 11/1999 | Rosenschein et al. |
| 5,997,528 A | 12/1999 | Bisch et al. |
| 6,010,496 A | 1/2000 | Appelbaum et al. |
| 6,083,193 A | 7/2000 | Kadziauskas et al. |
| 6,086,598 A | 7/2000 | Appelbaum et al. |
| 6,117,126 A | 9/2000 | Appelbaum et al. |
| 6,155,975 A | 12/2000 | Urich et al. |
| 6,161,545 A | 12/2000 | Chow |
| 6,175,180 B1 | 1/2001 | Angelini et al. |
| 6,193,683 B1 | 2/2001 | Ludin et al. |
| 6,203,516 B1 | 3/2001 | Kepley |
| 6,251,113 B1 | 6/2001 | Appelbaum et al. |
| 6,261,297 B1 | 7/2001 | Kadziauskas et al. |
| 6,319,220 B1 | 11/2001 | Bylsma |
| 6,391,020 B1 | 5/2002 | Kurtz et al. |
| 6,391,042 B1 | 5/2002 | Cimino |
| 6,394,974 B1 | 5/2002 | Kadziauskas et al. |
| 6,425,883 B1 | 7/2002 | Urich et al. |
| 6,428,531 B1 | 8/2002 | Visuri et al. |
| 6,443,900 B2 | 9/2002 | Adachi et al. |
| 6,452,120 B1 | 9/2002 | Chen |
| 6,452,123 B1 | 9/2002 | Chen |
| 6,487,447 B1 | 11/2002 | Weimann et al. |
| 6,506,176 B1 | 1/2003 | Mittelstein et al. |
| 6,589,204 B1 | 7/2003 | Sussman et al. |
| 6,610,052 B2 * | 8/2003 | Furumoto .................. 606/9 |
| 6,629,948 B2 | 10/2003 | Rockley et al. |
| 6,699,212 B1 | 3/2004 | Kadziauskas et al. |
| 6,726,679 B1 | 4/2004 | Dick et al. |
| 6,733,491 B2 | 5/2004 | Kadziauskas et al. |
| 6,780,165 B2 * | 8/2004 | Kadziauskas et al. .......... 604/22 |
| 6,884,252 B1 | 4/2005 | Urich et al. |
| 6,890,332 B2 | 5/2005 | Truckai et al. |
| 6,896,674 B1 | 5/2005 | Woloszko et al. |
| 6,908,472 B2 | 6/2005 | Wiener et al. |
| 6,939,317 B2 | 9/2005 | Zacharias |
| 6,962,583 B2 | 11/2005 | Kadziauskas et al. |
| 7,077,820 B1 * | 7/2006 | Kadziauskas et al. .......... 604/22 |
| 7,169,123 B2 | 1/2007 | Kadziauskas et al. |
| 7,193,521 B2 | 3/2007 | Moberg et al. |
| 7,316,664 B2 | 1/2008 | Kadziauskas et al. |
| 7,485,106 B2 | 2/2009 | Kadziauskas et al. |
| 2001/0003155 A1 | 6/2001 | Kadziauskas et al. |
| 2001/0003295 A1 | 6/2001 | Langlotz et al. |
| 2001/0003385 A1 | 6/2001 | Ise |
| 2002/0052600 A1 | 5/2002 | Davison et al. |
| 2002/0072741 A1 | 6/2002 | Silwa et al. |
| 2002/0082793 A1 | 6/2002 | Kadziauskas et al. |
| 2004/0092921 A1 | 5/2004 | Kadziauskas et al. |
| 2004/0092922 A1 | 5/2004 | Kadziauskas et al. |
| 2004/0193182 A1 | 9/2004 | Yaguchi et al. |
| 2005/0054971 A1 | 3/2005 | Steen et al. |
| 2005/0209560 A1 | 9/2005 | Boukhny et al. |
| 2005/0209621 A1 | 9/2005 | Gordon et al. |
| 2005/0288665 A1 | 12/2005 | Woloszko |
| 2006/0149301 A1 | 7/2006 | Claus |
| 2006/0195077 A1 * | 8/2006 | Kadziauskas et al. ............ 606/4 |
| 2006/0264809 A1 | 11/2006 | Hansmann et al. |
| 2007/0056596 A1 | 3/2007 | Fanney et al. |
| 2007/0073214 A1 | 3/2007 | Dacquay et al. |
| 2007/0078379 A1 | 4/2007 | Boukhny et al. |

FOREIGN PATENT DOCUMENTS

| | | |
|---|---|---|
| EP | 0270819 | 6/1988 |
| EP | 270819 A3 | 1/1989 |
| EP | 336620 A2 | 10/1989 |
| EP | 0336620 | 12/1993 |
| EP | 1351631 A1 | 10/2003 |
| EP | 1537840 | 6/2005 |
| JP | 02204337 | 8/1990 |
| JP | 5038343 A2 | 2/1993 |
| JP | 06183762 | 7/1994 |
| JP | 06189972 | 7/1994 |
| JP | 9313496 | 12/1997 |
| JP | 2001161740 | 6/2001 |
| JP | 2002087836 | 3/2002 |
| JP | 2002233534 A2 | 8/2002 |
| WO | WO 95/20374 | 3/1995 |
| WO | WO 98/08442 | 5/1998 |
| WO | WO 00/51508 | 9/2000 |
| WO | WO 00/64388 | 11/2000 |
| WO | WO 01/13838 | 1/2001 |
| WO | WO 02/056806 | 7/2002 |
| WO | WO 2005/092023 | 10/2005 |

OTHER PUBLICATIONS

Taylor, Intraoperative troubleshooting of an advanced phacoemulsification system, The Surgial Technologist, Mar. 1985, pp. 11-14, 17 (2), Association of Surgical Technologists, Rochester, MI.

Pulsar cuts phaco time, boots efficiency in cataract removal; Ophthalmology Times: Aug. 15, 1986; 1 page, 11 (16), Harcourt Brace Jovanovich, Inc.

Ocusystem Operation Manual, May 1995, 79 pages.

* cited by examiner

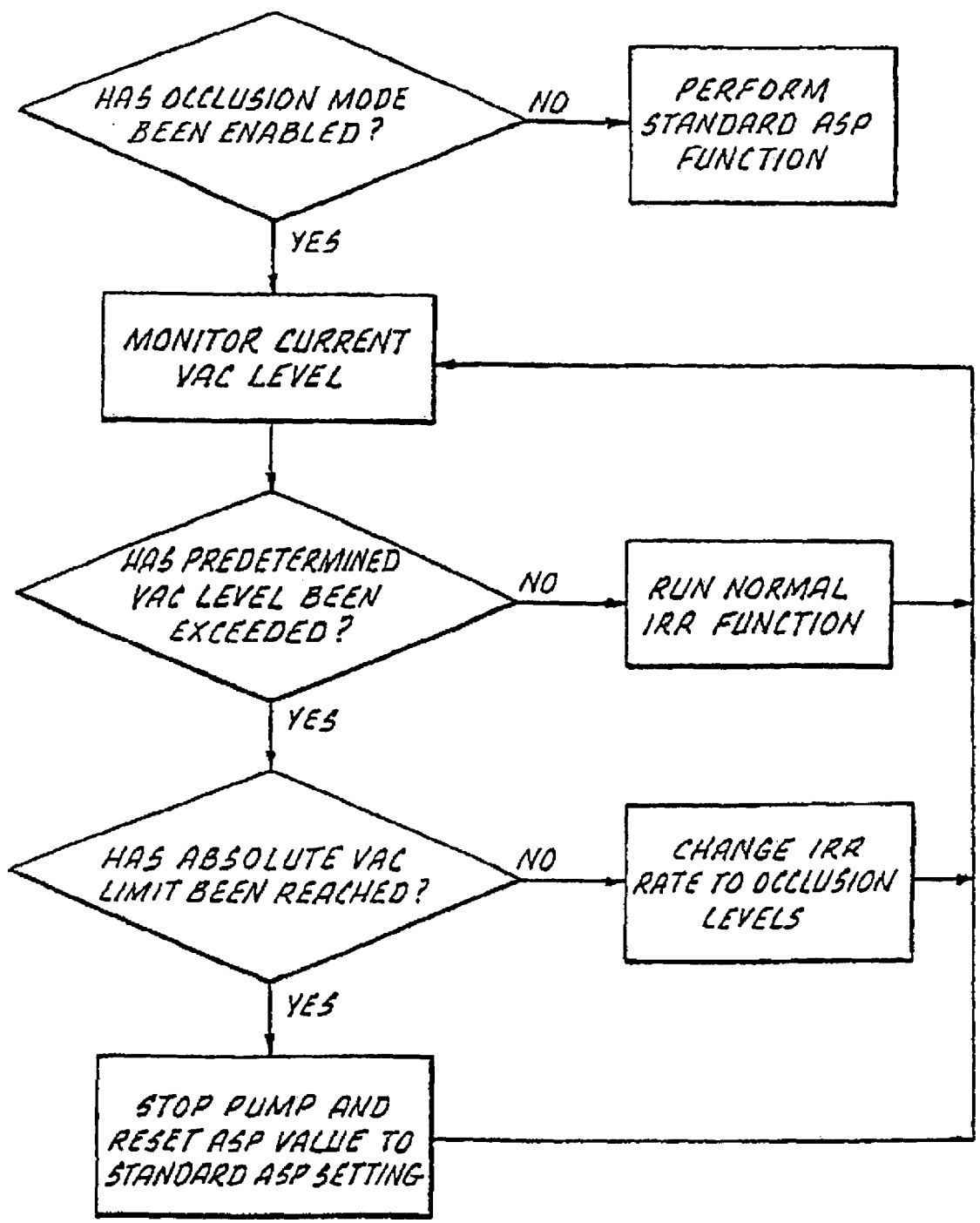
_Fig. 6._

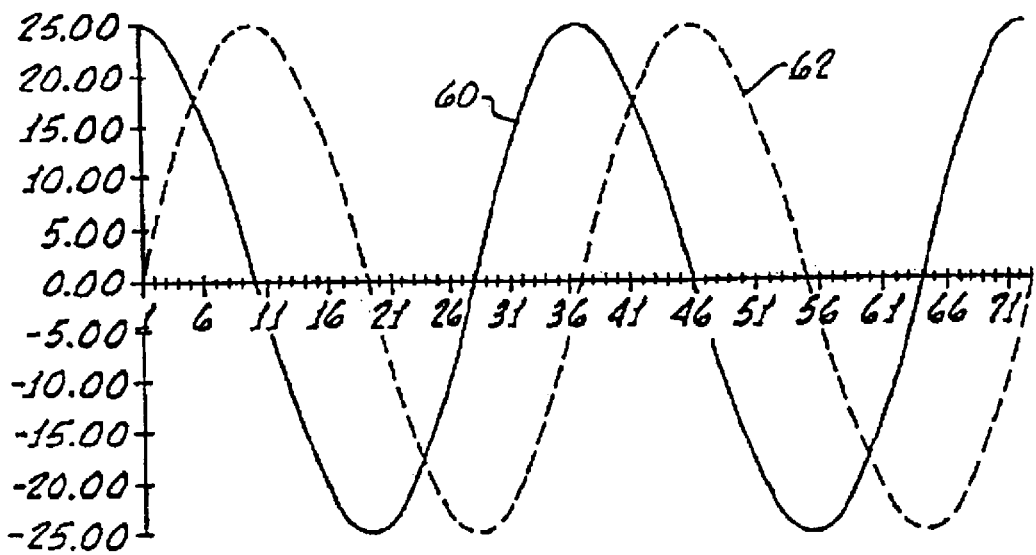
_Fig. 7._
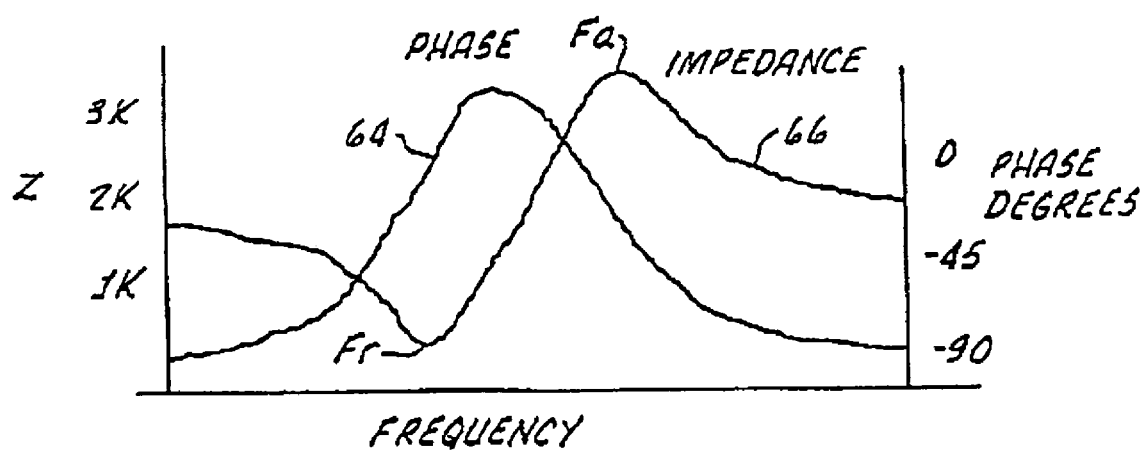
_Fig. 8._

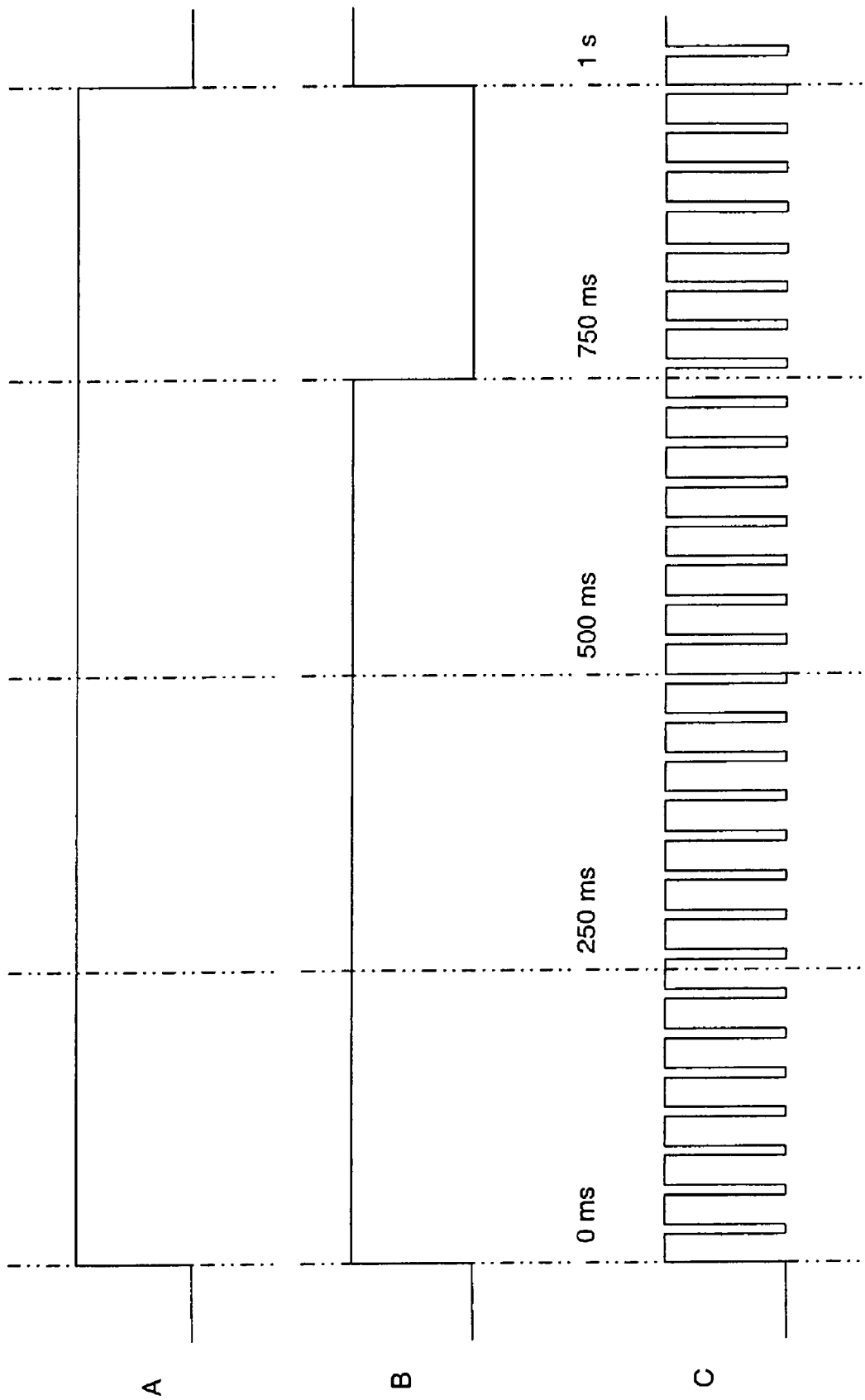

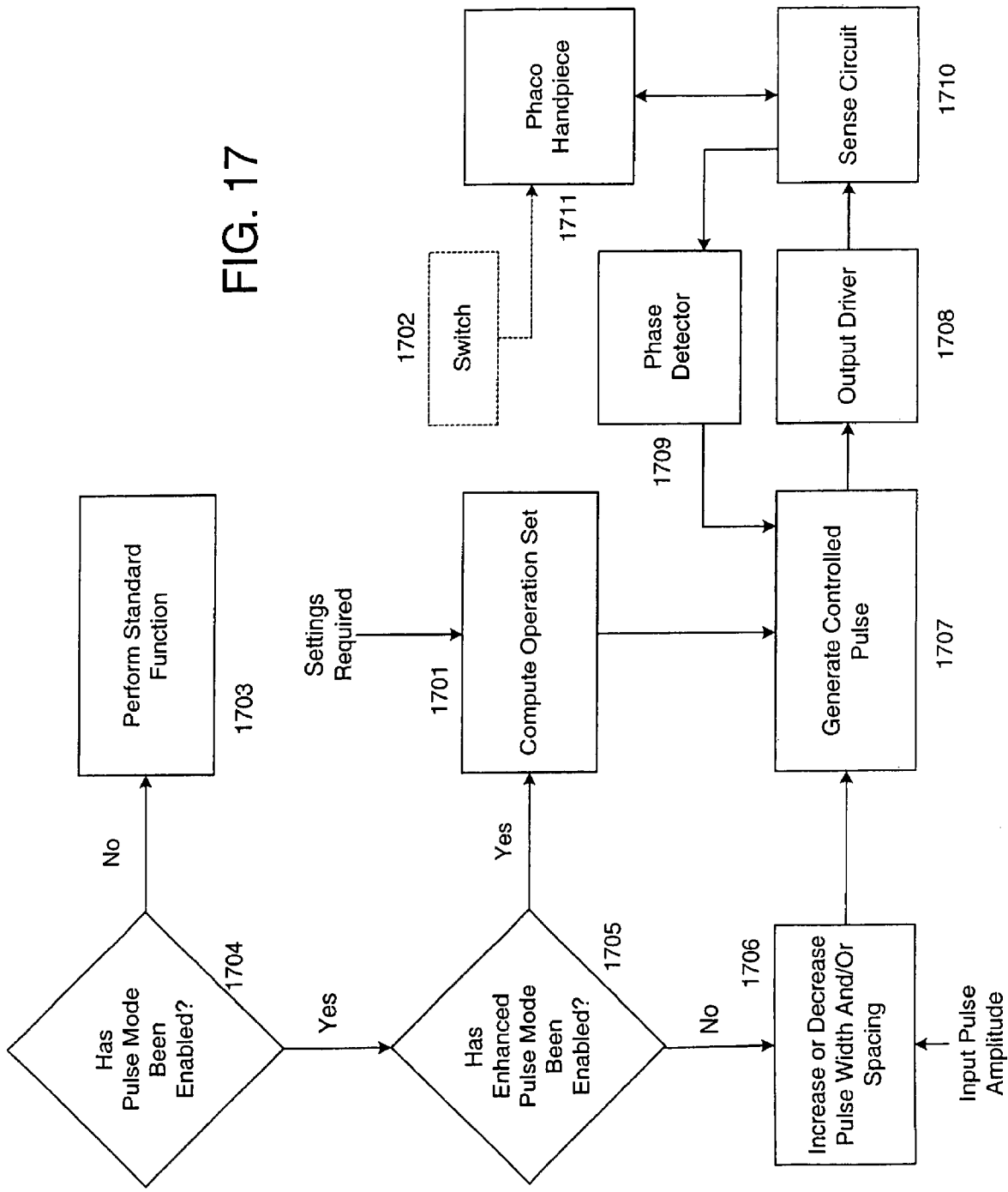

Occlusion Sensed →

ENHANCED MICROBURST ULTRASONIC POWER DELIVERY SYSTEM AND METHOD

This application is a continuation of copending U.S. patent application Ser. No. 10/278,775, entitled "Novel Enhanced Microburst Ultrasonic Power Delivery System and Method," inventors Kenneth E. Kadziauskas et al, filed Oct. 21, 2002, the entirety of which is hereby incorporated by reference.

BACKGROUND OF THE INVENTION

1. Field of the Invention

The present invention relates generally to the field of surgical tissue removal systems, and more specifically to enhanced ultrasonic power delivery during surgical procedures such as phacoemulsification.

2. Description of the Related Art

Phacoemulsification surgery has been successfully employed in the treatment of certain ocular problems, such as cataracts. Phacoemulsification surgery utilizes a small corneal incision to insert the tip of at least one phacoemulsification handheld surgical implement, or handpiece. The handpiece includes a needle which is ultrasonically driven once placed within an incision to emulsify the eye lens, or break the cataract into small pieces. The broken cataract pieces may subsequently be removed using the same handpiece or another handpiece in a controlled manner. The surgeon may then insert lens implants in the eye through the incision. The incision is allowed to heal, and the results for the patient are typically significantly improved eyesight.

As may be appreciated, the flow of fluid to and from a patient through a fluid infusion or extraction system and power control of the phacoemulsification handpiece is critical to the procedure performed. Different medically recognized techniques have been utilized for the lens removal portion of the surgery. Among these, one popular technique is a simultaneous combination of phacoemulsification, irrigation and aspiration using a single handpiece. This method includes making the incision, inserting the handheld surgical implement to emulsify the cataract or eye lens. Simultaneously with this emulsification, the handpiece provides a fluid for irrigation of the emulsified lens and a vacuum for aspiration of the emulsified lens and inserted fluids.

Currently available phacoemulsification systems include a variable speed peristaltic pump, a vacuum sensor, an adjustable source of ultrasonic power, and a programmable microprocessor with operator-selected presets for controlling aspiration rate, vacuum and ultrasonic power levels. A phacoemulsification handpiece is interconnected with a control console by an electric cable for powering and controlling the piezoelectric transducer. Tubing provides irrigation fluid to the eye and enables withdrawal of aspiration fluid from an eye through the handpiece. The hollow needle of the handpiece may typically be driven or excited along its longitudinal axis by the piezoelectric effect in crystals created by an AC voltage applied thereto. The motion of the driven crystal is amplified by a mechanically resonant system within the handpiece such that the motion of the needle connected thereto is directly dependent upon the frequency at which the crystal is driven, with a maximum motion occurring at a resonant frequency. The resonant frequency is dependent in part upon the mass of the needle interconnected therewith, which is typically vibrated by the crystal.

From the standpoint of the electronics employed in phacoemulsification surgery, for purely capacitive circuits, a 90 degree phase angle exists between a sine wave representing the voltage applied to the handpiece and the resultant current provided to the handpiece. This phase angle is expressed as −90 degrees. For a purely inductive circuit, the phase angle equals +90 degrees and for purely resistive circuits the phase angle equals zero.

A typical range of frequency used for phacoemulsification handpiece is between about 25 kHz to about 50 kHz. A frequency window exists for each phacoemulsification handpiece that can be characterized by specific handpiece impedance and phase. The aforementioned frequency window is bounded by an upper frequency and a lower cutoff frequency. The center of this window is typically the point where the handpiece electrical phase reaches a maximum value. At frequencies outside of this window, the electrical phase of the handpiece is equal to −90 degrees.

Handpiece power transfer efficiency is given by the formula $(V^*I)(COS \Phi)$, where $\Phi$ is the aforementioned phase angle. Using this power transfer efficiency equation, the most efficient handpiece operating point occurs when the phase is closest to 0 degrees. Thus optimum handpiece power transfer efficiency requires controlling power frequency to achieve a phase value as close to zero degrees as possible. Achieving this goal is complicated by the fact that the phase angle of the ultrasonic handpiece also depends on transducer loading. Transducer loading occurs through the mechanically resonant handpiece system, including the needle. Contact by the needle with tissue and fluids within the eye create a load on the piezoelectric crystals with concomitant change in the operating phase angle.

Consequently, phase angles are determined and measured at all times during operation of the handpiece to adjust the driving circuitry, achieve an optimum phase angle, and effect constant energy transfer into the tissue by the phacoemulsification handpiece. Automatic tuning of the handpiece may be provided by monitoring the handpiece electrical signals and adjusting the frequency to maintain consistency with selected parameters. Control circuitry for a phacoemulsification handpiece can include circuitry for measuring the phase between the voltage and the current, typically identified as a phase detector. Difficulties may arise if phase shift is measured independent of the operating frequency of the phacoemulsification handpiece, because phase shift depends on handpiece operating frequency, and time delay in the measurement thereof requires complex calibration circuitry to provide for responsive tuning of the handpiece.

Power control of the phacoemulsification handpiece is therefore highly critical to successful phacoemulsification surgery. Certain previous systems address the requirements of power control for a phacoemulsification handpiece based on the phase angle between voltage applied to a handpiece piezoelectric transducer and the current drawn by the piezoelectric transducer and/or the amplitude of power pulses provided to the handpiece. The typical arrangement is tuned for the particular handpiece, and power is applied in a continuous fashion or series of solid bursts subject to the control of the surgeon/operator. For example, the system may apply power for 150 ms, then cease power for 350 ms, and repeat this on/off sequence for the necessary duration of power application. In this example, power is applied through the piezoelectric crystals of the phacoemulsification handpiece to the needle causing ultrasonic power emission for 150 ms, followed by ceasing application of power using the crystals, handpiece, and needle for 350 ms. It is understood that while power in this example is applied for 150 ms, this application of power includes application of a sinusoidal waveform to the piezoelectric crystals at a frequesncy of generally between about 25 kHz and 50 kHz and is thus not truly "constant." Application of power during this 150 ms period is defined as a constant application of a 25 kHz to 50 kHz sinusoid. In certain circumstances, the surgeon/operator may wish to apply these power bursts for a duration of time, cease application of power, then reapply at this or another power setting. The frequency and duration of the burst is typically controllable, as is the length of the stream of bursts applied to the affected area. The time period where power is not applied enable cavitation in the affected area whereby broken sections may be removed using aspiration provided by the handpiece or an aspiration apparatus.

Additionally, the surgeon operator may wish to employ certain known procedures, such as a "sculpt" procedure to break the lens, or a "chop" procedure to collect the nucleus and maintain a strong hold on the broken pieces. These specialized "chop or quadrant removal" procedures typically entail applying power or energy in a constant span of anywhere from approximately 50 milliseconds to 200 milliseconds in duration.

The on/off application of power facilitates breaking the cataract into pieces and relatively efficient removal thereof. The ultrasonically driven needle in a phacoemulsification handpiece becomes warm during use, resulting from frictional heat due in part to mechanical motion of the phacoemulsification handpiece tip. In certain circumstances, it has been found that the aforementioned method of applying power to the affected region in a continuous mode can produce a not insignificant amount of heat in the affected area. Irrigation/aspiration fluids passing through the needle may be used to dissipate this heat, but care must be taken to avoid overheating of eye tissue during phacoemulsification, but in certain procedures fluid circulation may not dissipate enough heat. The risk of damaging the affected area via application of heat can be a considerable negative side effect.

Further, the application of power in the aforementioned manner can in certain circumstances cause turbulence and/or chatter, as well as cause significant flow issues, such as requiring considerable use of fluid to relieve the area and remove particles. Also, the application of constant groups of energy can cause nuclear fragments to be pushed away from the tip of the handpiece because of the resultant cavitation from the energy applied. Collecting and disposing of fragments in such a cavitation environment can be difficult in many circumstances. These resultant effects are undesirable and to the extent possible should be minimized.

Based on the foregoing, it would be beneficial to provide a system which did not include certain drawbacks associated with previous tissue removal systems, such as phacoemulsification systems.

SUMMARY OF THE INVENTION

According to a first aspect, there is provided a method for delivering energy during a surgical procedure. The method comprises applying energy during at least one pulsed energy on period. Applying energy during the pulsed energy on period comprises applying energy during a series of short burst periods, said short burst periods interspersed by short rest periods wherein minimal energy is applied, and refraining from delivering energy during a long off period, the long off period comprising a relatively long period when minimal energy is applied, wherein one long off period follows each pulsed energy on period. The short burst periods and the short rest periods are relatively brief in duration as compared with the long off period.

According to a second aspect, there is provided a method of delivering ultrasonic energy during a tissue removal procedure. The method comprises delivering pulses of energy during an on period, energy pulse delivery comprising delivering at least one relatively short burst of energy, and pausing for at least one relatively short period. The method further comprises pausing for a relatively long off period after said on period and prior to commencing any subsequent on period, wherein pausing for each relatively short period and for the relatively long off period comprises applying minimal energy therein.

According to a third aspect, there is provided a surgical apparatus, comprising means for applying energy during at least one pulsed energy on period. The energy applying means comprise means for bursting energy during a series of short burst periods, said short burst periods interspersed by short rest periods wherein minimal energy is applied, and means for refraining from delivering energy during a long off period, the long off period comprising a relatively long period when minimal energy is applied. One long off period follows each pulsed energy on period. The short burst periods and short rest periods are relatively brief in duration as compared with the long off period.

According to a fourth aspect, there is provided a method for providing ultrasonic energy to an ocular region during a phacoemulsification procedure. The method comprises applying energy to the ocular region during at least one pulsed energy on period followed by a long off period, wherein applying energy to the ocular region during the pulsed energy on period comprises applying energy to the ocular region during the phacoemulsification procedure in a series of short burst periods having duration of at most approximately ten milliseconds. The short burst periods are interspersed by short rest periods, said short rest periods having minimal power application for at most approximately twenty five milliseconds.

According to a fifth aspect, there is provided an apparatus comprising a handpiece having a needle and electrical means for ultrasonically vibrating said needle, power source means for providing pulsed electrical power to the handpiece electrical means, input means for enabling an operator to select an amplitude of the electrical pulses, means for providing irrigation fluid to the eye and aspirating fluid from the handpiece needle, and control means for controlling power supplied to the handpiece during a surgical procedure. The control means control power supplied by applying power during at least one pulsed energy on period followed by at least one long off period, the pulsed energy on period comprising a series of short burst periods having duration of at most approximately ten milliseconds. The short burst periods are interspersed by short rest periods of minimal amplitude, the short rest periods having duration of at most approximately twenty five milliseconds.

According to a sixth aspect, there is provided an apparatus comprising a handpiece having a needle and electrical means for ultrasonically vibrating said needle, power source means for providing pulsed electrical power to the handpiece electrical means, input means for enabling an operator to select an amplitude of the electrical pulses, means for providing irrigation fluid to the eye and aspirating fluid from the handpiece needle, and control means for controlling power supplied to the handpiece. The control means control power supplied by applying power during at least one pulsed energy on period, wherein applying power during the pulsed energy on period comprises applying power during a series of short burst periods. The short burst periods are interspersed by short rest periods, and the control means further deliver de minimis power during a long off period, the long off period comprising a relatively long period when de minimis power is applied, and one long off period following each pulsed energy on period.

According to a seventh aspect, there is provided a method for delivering energy during a surgical procedure. The method comprises applying energy during at least one pulsed energy on period, wherein applying energy during the pulsed energy on period comprises applying energy during a series of short burst periods, the short burst periods interspersed by short rest periods, and refraining from delivering energy during a long off period, the long off period comprising a relatively long period when a minimal level of energy is applied, wherein one long off period follows each pulsed energy on period. The short burst periods and the short rest periods are relatively brief in duration as compared with said long off period.

According to an eighth aspect, there is provided a method of delivering ultrasonic energy during an ocular nodule surgical procedure. The method comprises delivering pulses of energy during an on period, energy pulse delivery comprising delivering at least one relatively short burst of energy, and pausing for at least one relatively short period. The method further comprises pausing for a relatively long off period after said on period and prior to commencing any subsequent on period, wherein pausing for each relatively short period and for the relatively long off period comprises applying minimal energy therein.

According to a ninth aspect, there is provided a method for delivering energy to a handpiece during a surgical procedure. The method comprises providing energy to the handpiece over a plurality of alternating energy on and energy off periods, and during at least one of the energy on periods applying energy as a series of short energy bursts interspersed with short rest periods of minimal energy application. The method further comprises, during the energy off periods, delivering a minimal level of energy, the short energy bursts and the short rest periods being shorter in duration than any one of the energy off periods.

These and other objects and advantages of all aspects of the present invention will become apparent to those skilled in the art after having read the following detailed disclosure of the preferred embodiments illustrated in the following drawings.

DESCRIPTION OF THE DRAWINGS

The present invention is illustrated by way of example, and not by way of limitation, in the figures of the accompanying drawings in which:

FIG. 6 is a flow chart illustrating the operation of the occluded-unoccluded mode of the phacoemulsification system with variable irrigation rates;

FIG. 7 is a plot of the 90 degree phase shift between the sine wave representation of the voltage applied to a piezoelectric phacoemulsification handpiece and the resultant current into the handpiece;

FIG. 8 is a plot of the phase relationship and the impedance of a typical piezoelectric phacoemulsification handpiece;

FIGS. 16A, 16B, and 16C illustrate variations of the ultrasonic energy waveform delivery and control according to the present invention;

FIG. 17 presents a conceptual block diagram of computation and delivery of the enhanced ultrasonic energy waveform of the present invention;

DETAILED DESCRIPTION OF THE INVENTION

Device.

Figure 1:
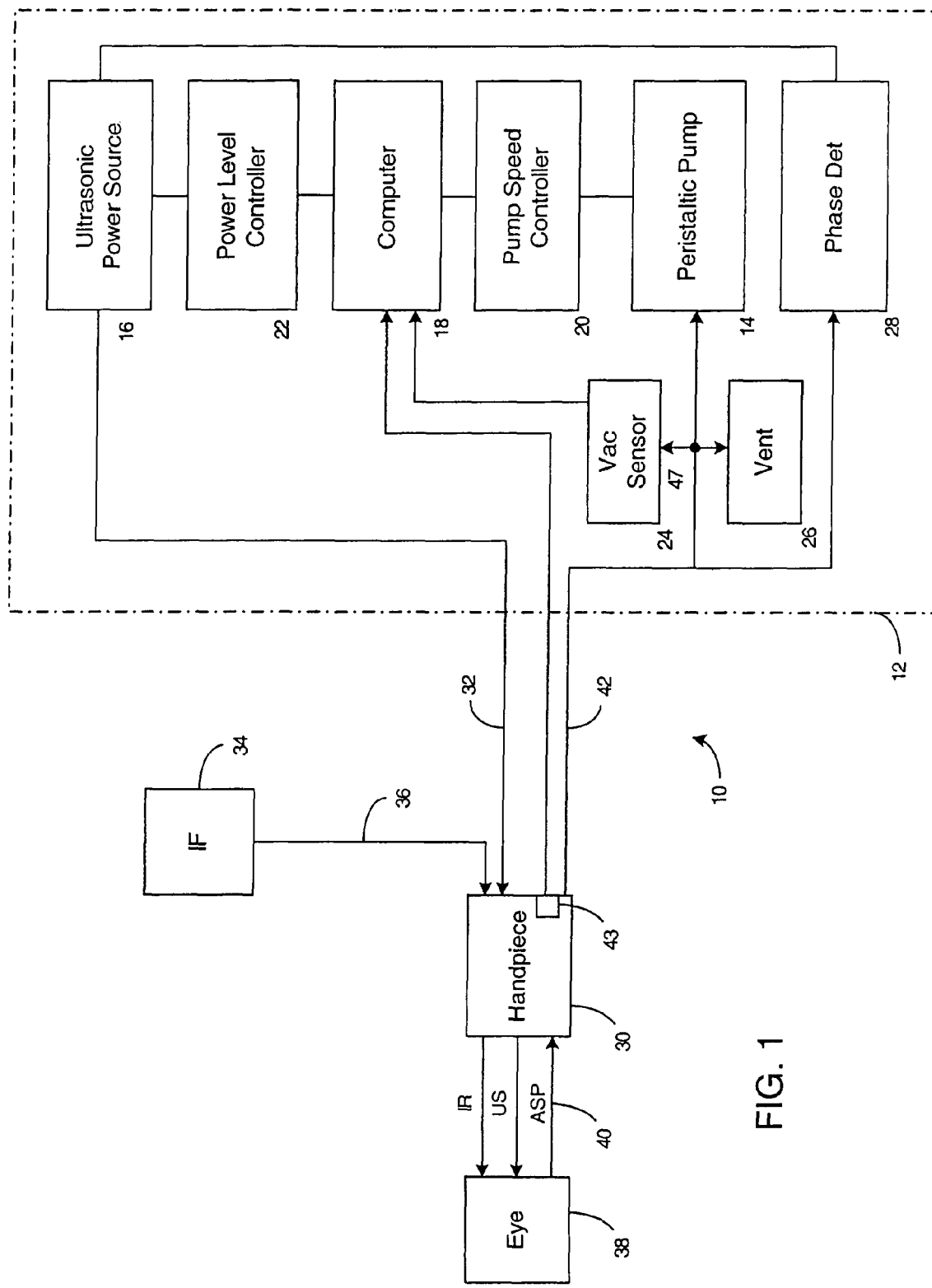
FIG. 1 is a functional block diagram of a phacoemulsification system in accordance with an aspect of the present invention.

FIG. 1 illustrates a phacoemulsification system in block diagram form, indicated generally by the reference numeral 10. The system has a control unit 12, indicated by the dashed lines in FIG. 1 which includes a variable speed peristaltic pump 14, which provides a vacuum source, a source of pulsed ultrasonic power 16, and a microprocessor computer 18 that provides control outputs to pump speed controller 20 and ultrasonic power level controller 22. A vacuum sensor 24 provides an input to computer 18 representing the vacuum level on the input side of peristaltic pump 14. Suitable venting is provided by vent 26.

A phase detector 28 provides an input to computer 18 representing a phase shift between a sine wave representation of the voltage applied to a handpiece/needle 30 and the resultant current into the handpiece 30. The block representation of the handle 30 includes a typical handpiece having a needle and electrical means, typically a piezoelectric crystal, for ultrasonically vibrating the needle. The control unit 12 supplies power on line 32 to a phacoemulsification handpiece/needle 30. An irrigation fluid source 34 is fluidly coupled to handpiece/needle 30 through line 36. The irrigation fluid and ultrasonic power are applied by handpiece/needle 30 to a patient's eye, or affected area or region, indicated diagrammatically by block 38. Alternatively, the irrigation source may be routed to the eye 38 through a separate pathway independent of the handpiece. The eye 38 is aspirated by the control unit peristaltic pump 14 through lines 40 and 42. A switch 43 disposed on the handpiece 30 may be utilized as a means for enabling a surgeon/operator to select an amplitude of electrical pulses to the handpiece via the computer 18, power level controller 22 and ultrasonic power source 16 as discussed herein. Any suitable input means, such as, for example, a foot pedal (not shown) may be utilized in lieu of the switch 43.

Figure 2:
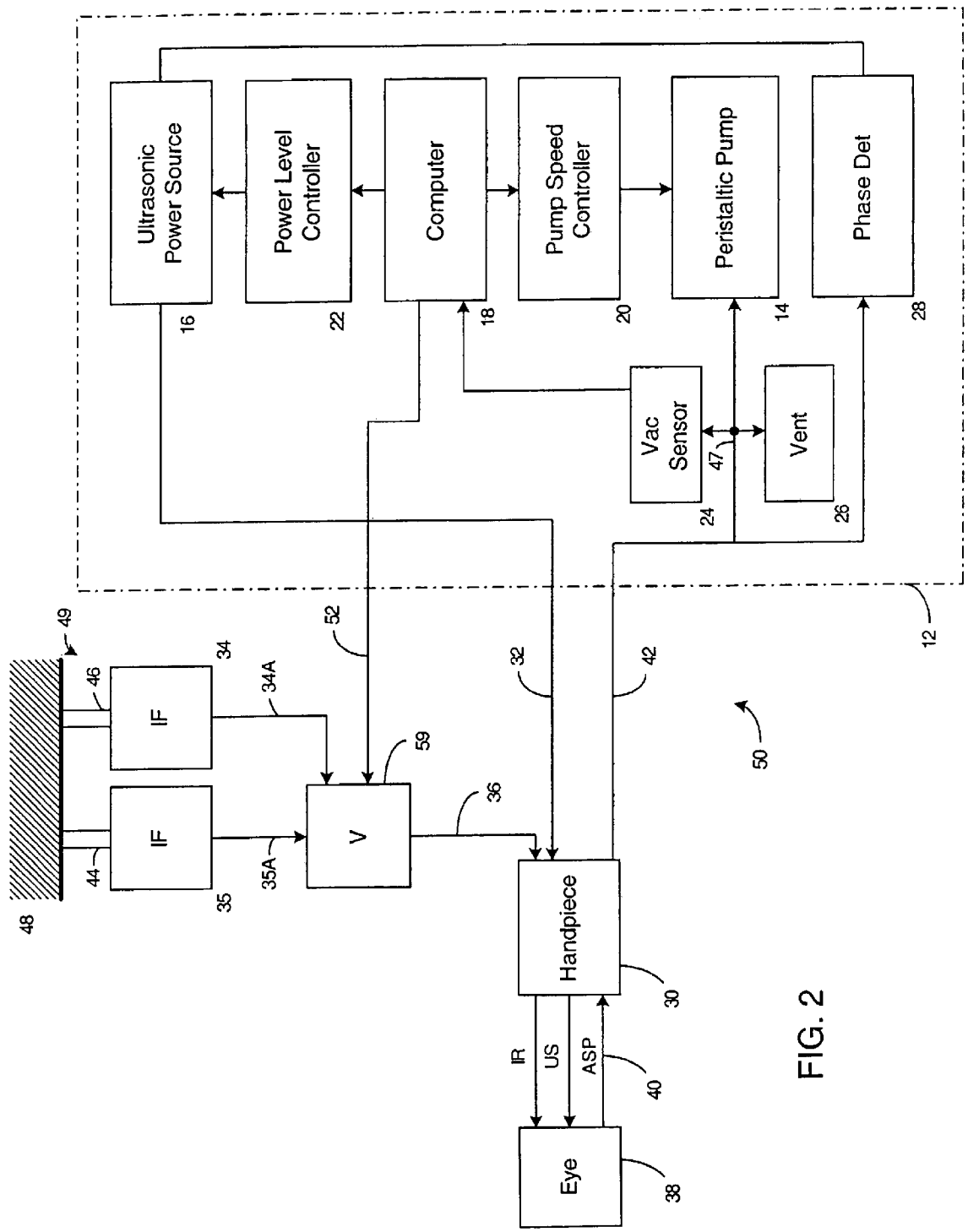
FIG. 2 is a functional block diagram of an alternative aspect of a phacoemulsification system including apparatus for providing irrigation fluid at more than one pressure to a handpiece.

FIG. 2 shows an alternative phacoemulsification system 50 incorporating all of the elements of the system 10 shown in FIG. 1, with identical reference characters identifying components, as shown in FIG. 1. In addition to the irrigation fluid source 34, a second irrigation fluid source 35 is provided with the sources 34, 35 being connected to the line 36 entering the handpiece/needle 30 through lines 34*a*, 35*a*, respectively, and to a valve 59. The valve 59 functions to alternatively connect line 34A and source 34 and line 35A and source 35 with the handpiece/needle 30 in response to a signal from the power level controller 22 through a line 52.

As shown, irrigation fluid sources 34, 35 are disposed at different heights above the handpiece/needle 30 providing a means for introducing irrigation fluid to the handpiece at a plurality of pressures, the head of the fluid in the container 35 being greater than the head of fluid in the container 34. A harness 49, including lines of different lengths 44, 46, when connected to the support 48, provides a means for disposing the containers 34, 35 at different heights over the handpiece/needle 30.

The use of containers for irrigation fluids at the various heights is representative of the means for providing irrigation fluids at different pressures, and alternatively, separate pumps may be provided with, for example, separate circulation loops (not shown). Such containers and pumps can provide irrigation fluid at discrete pressures to the handpiece/needle 30 upon a command from the power controller 22.

Operation.

Figure 3:
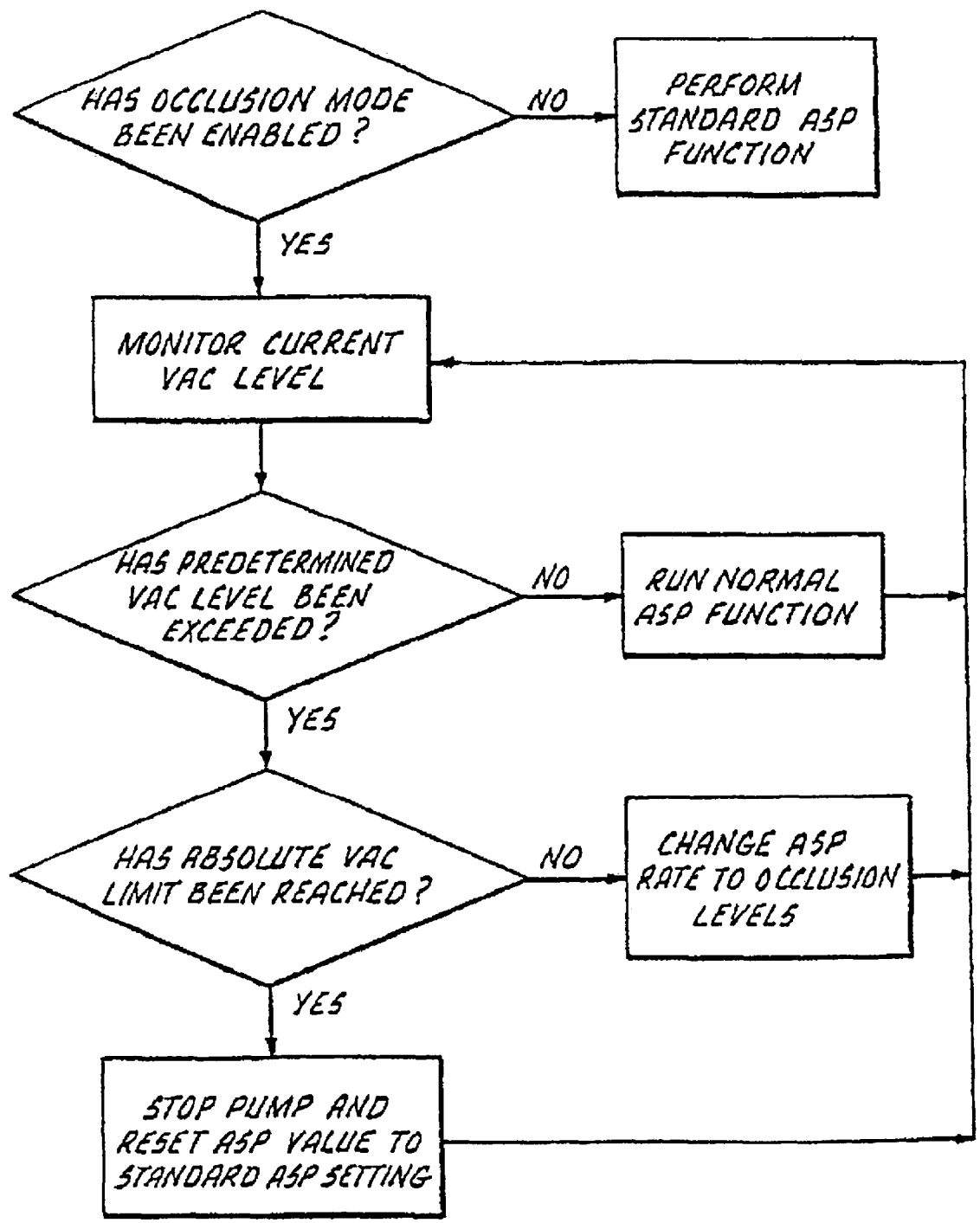
FIG. 3 is a flow chart illustrating the operation Of the occluded-unoccluded mode of the phacoemulsification system with variable aspiration rates.

The computer 18 responds to preset vacuum levels in input line 47 to peristaltic pump 14 by means of signals from the previously mentioned vacuum sensor 24. Operation of the control unit in response to the occluded-unoccluded condition of handpiece 30 is shown in the flow diagram of FIG. 3. As shown in FIG. 3, if the handpiece aspiration line 40 becomes occluded, the vacuum level sensed by vacuum sensor 24 may increase. The computer 18 may provide operator-settable limits for aspiration rates, vacuum levels and ultrasonic power levels. As illustrated in FIG. 3, when the vacuum level sensed by vacuum sensor 24 reaches a predetermined level as a result of occlusion of the handpiece aspiration line 40, computer 18 provides signals to pump speed controller 20 to change the speed of the peristaltic pump 14 which, in turn, changes the aspiration rate. Depending upon the characteristics of the material occluding handpiece/needle 30, the speed of the peristaltic pump 14 can either be increased or decreased. When the occluding material is broken up, the vacuum sensor 24 registers a drop in vacuum level, causing computer 18 to change the speed of peristaltic pump 14 to an unoccluded operating speed.

Figure 4:
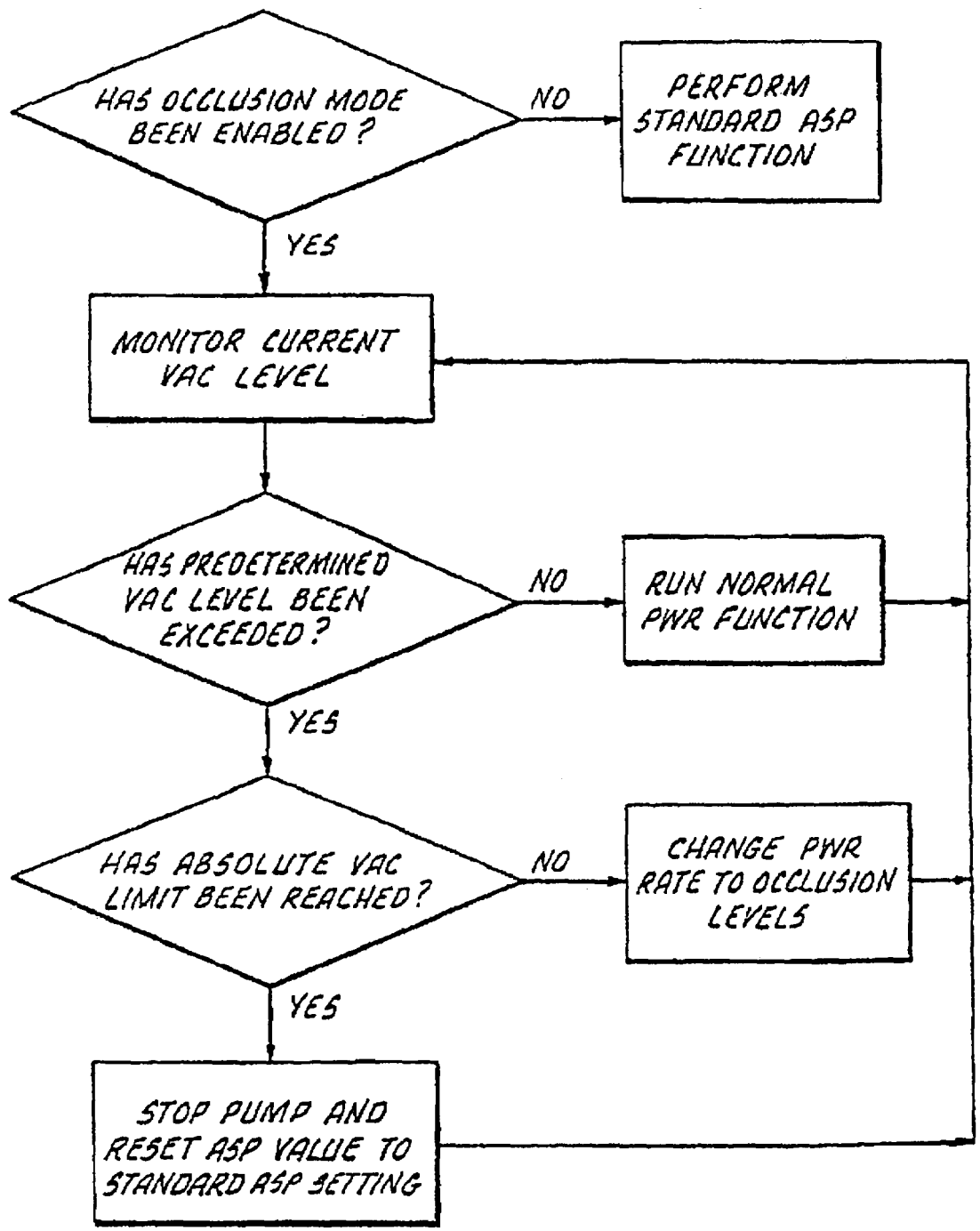
FIG. 4 is a flow chart illustrating the operation Of the occluded-unoccluded-mode of the phacoemulsification system with variable ultrasonic power levels.

In addition to changing the phacoemulsification parameter of aspiration rate by varying the speed of the peristaltic pump 14, the power level of the ultrasonic power source 16 can be varied as a function of the occluded or unoccluded condition of handpiece 30. FIG. 4 illustrates in flow diagram form a basic form of control of the ultrasonic power source power level using computer 18 and power level controller 22. The flow diagram of FIG. 4 corresponds to the flow diagram of FIG. 3 but varies the phacoemulsification parameter of the ultrasonic power level.

The impedance of the typical phacoemulsification handpiece varies with frequency, or in other words, the handpiece is reactive. Dependence of typical handpiece phase and impedance as a function of frequency is shown in FIG. 8. In FIG. 8, curve 64 represents the phase difference between current and voltage of the handpiece as function frequency and curve 66 shows the change in impedance of the handpiece as a function of frequency. The impedance exhibits a low at "Fr" and a high "Fa" for a typical range of frequencies, such as in the range of approximately 25 kHz to approximately 50 kHz.

Automatic tuning of the handpiece typically requires monitoring the handpiece electrical signals and adjusting the frequency to maintain a consistency with selected parameters. To compensate for a load occurring at the tip of the phacoemulsification handpiece, the drive voltage to the handpiece can be increased while the load is detected and then decreased when the load is removed. This phase detector is typically part of the controller in this type of system. In such conventional phase detectors, the typical output is a voltage as proportional to the difference in alignment of the voltage and the current waveform, for example, −90 degrees as shown in FIG. 7. As shown in FIG. 8, while using the handpiece, the waveform varies in phase and correspondingly the output waveform also varies.

Heretofore, the standard technique for measuring electrical phase has been to read a voltage proportional to phase and also to frequency. This type of circuit may be calibrated for use-with a single frequency. Changing the frequency may cause the calibration data to be incorrect. As also seen in single frequency systems, corrected phase value will drift due to variation in the circuit parameters.

Figure 9:
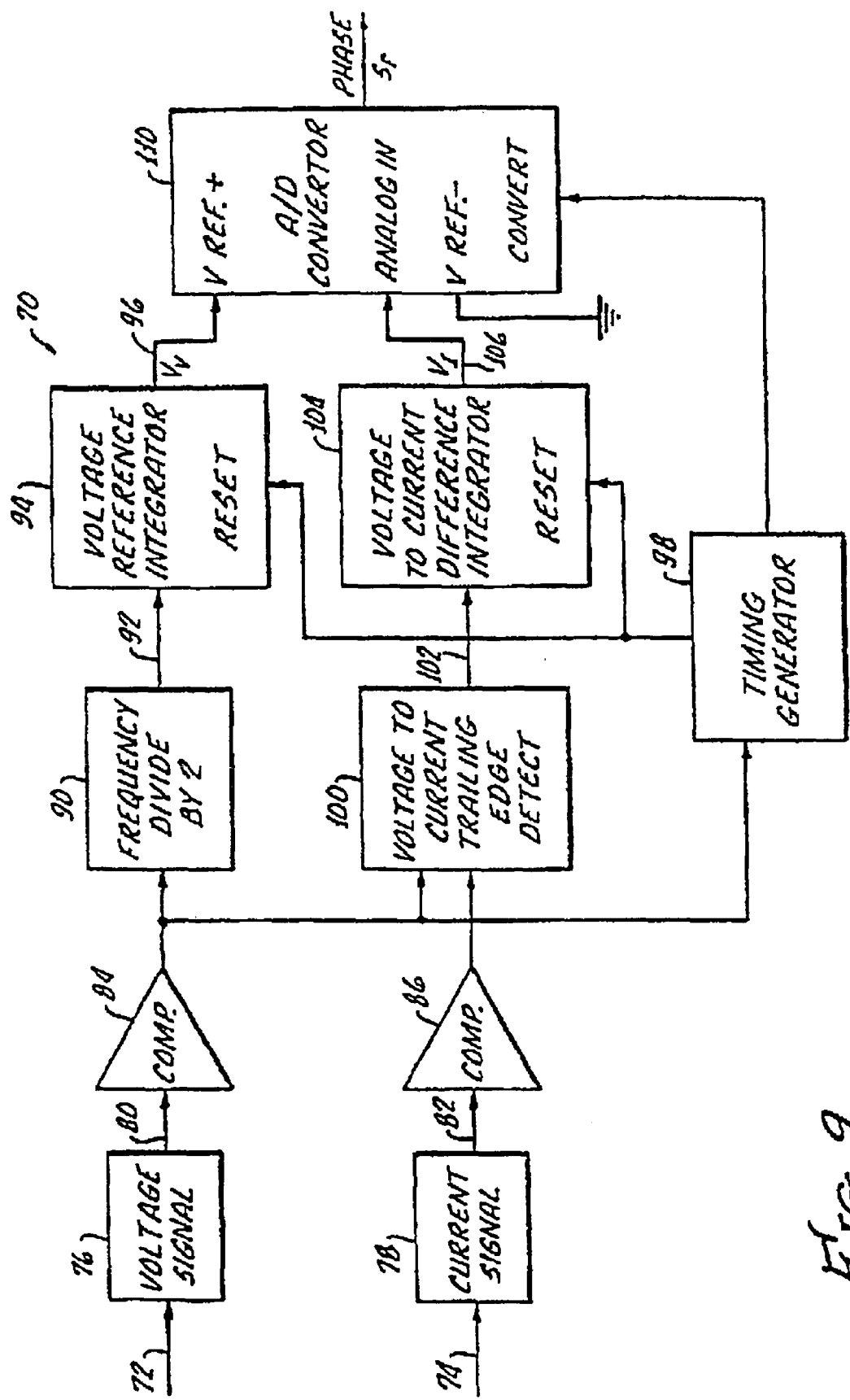
FIG. 9 is a block diagram of improved phase detector circuitry suitable for performing a method in accordance with the present invention.

One other available approach utilizes a microprocessor to compare the value of the phase detector output with that of a frequency detector and compute the true phase. This approach is fairly complex and is subject to drift of the individual circuits as well as resolution limitations. A block diagram 70 as shown in FIG. 9 is representative of an improved phase detector suitable for performing in accordance with the design. Each of the function blocks shown comprises conventional state-of-the-art circuitry of typical design and components for producing the function represented by each block as hereinafter described.

The system converts voltage input 72 and current 74 from a phacoemulsification handpiece 30 to an appropriate signal using an attenuator 76 on the voltage signal to the phacoemulsification handpiece, and a current sense resistor 78 and fixed gain amplifier for the handpiece 30 current. Thereafter, the system passes an AC voltage signal 80 and AC current signal 82 to comparators 84, 86 which convert the analog representations of the phacoemulsification voltage and current to logic level clock signals.

The system feeds output from the comparator 84 into a D flip flop integrated circuit 90 configured as a frequency divide by 2. The system then feeds output 92 of the integrated circuit 90 into an operational amplifier configured as an integrator 94. The output 96 of the integrator 94 is a sawtooth waveform of which the final amplitude is inversely proportional to the handpiece frequency. A timing generator 98 uses a clock synchronous with the voltage signal to generate A/D converter timing, as well as timing to reset the integrators at the end of each cycle. The system feeds this signal into the voltage reference of an A/D converter via line 96.

The voltage leading edge to current trailing edge detector 100 uses a D flip flop integrated circuit to isolate the leading edge of the handpiece voltage signal. This signal is used as the initiation signal to start the timing process between the handpiece 30 voltage and handpiece 30 current. The output 102 of the leading edge to current trailing edge detector 100 is a pulse proportional to the time difference in occurrence of the leading edge of the handpiece 30 voltage waveform and the falling edge of the handpiece current waveform.

The system uses another integrator circuit 104 for the handpiece phase signal 102 taken from the leading edge to current trailing edge detector 100. Output 106 of the integrator circuit 104 is a sawtooth waveform in which the peak amplitude is proportional to the time difference in the onset of leading edge of the phacoemulsification voltage and the trailing edge of the onset of the handpiece current waveform. The system feeds output 106 of the integrator circuit 104 into the analog input or an A/D (analog to digital converter) integrated circuit 110. The positive reference input 96 to the A/D converter 110 is a voltage that is inversely proportional to the frequency of operation. The phase voltage signal 96 is proportional to the phase difference between the leading edge of the voltage onset, and the trailing edge of the current onset, as well as inversely proportional to the frequency of operation. In this configuration, the two signals frequency voltage reference 96 and phase voltage 106 track each other over the range of frequencies, so that the output of the A/D converter 110 produces the phase independent of the frequency of operation.

In this arrangement, the system computer 18 (see FIGS. 1 and 2) is provided with a real time digital phase signal wherein 0 to 255 counts will consistently represent 0 to 359 degrees of phase. No form of calibration is necessary since the measurements are consistent despite the frequencies utilized. For example, using AMPs operation frequencies of 38 kHz and 47 kHz and integrator having a rise time of $150 \times 10^5$ V/sec and an 8 bit A/D converter having 256 counts, a constant ratio is maintained and variation in frequency does not affect the results. This shown in the following examples.

EXAMPLE 1

38 KHz Operation

Period of 1 clock cycle=1/F@38 KHz=26.32 times $10^{-6}$ S

Portion of one period for I=90 deg=26.32 times $10^{-6}$ S Divided by 4=6.59 times $10^{-6}$ S Integrator output for one reference cycle=(150 times $10^3$ V/S) times (26.32 times $10^{-6}$ S)=3.95 Volts Integrator output from 90 degree cycle duration=(150 times $10^3$ V/S) times (6.59 times $10^{-6}$ S)=0.988 Volts Resulting Numerical count from A/D converter=3.95 Volts/256 counts=0.0154 Volts per count Actual Number of A/D counts for 90 deg at 38 KHz=0.988/0.0154=64 counts

Example 2

47 KHz Operation

Period of 1 clock cycle=1/F@47 KHz=21.28 times $10^{-6}$ S

Portion of one period for I=90 deg=21.28 times $10^{-6}$ S Divided by 4=5.32 times $10^{-6}$ S Integrator output for one reference cycle=(150 times $10^3$ V/S) times (21.28 times $10^{-6}$ S)=3.19 volts Integrator output from 90 degree cycle duration=(150 times $10^3$ V/S) times (5.32 times $10^{-6}$ S)=0.798 Volts Resulting Numerical count from A/D converter=3.19 Volts/256 counts=0.0124 Volts per count Actual Number of A/D counts for 90 deg at 47 KHz=0.798/0.0124=64 counts This represents the baseline operation of the present system, namely the ability to tune the phacoemulsification handpiece to a generally acceptable level.

Basic Operation.

Figure 5:
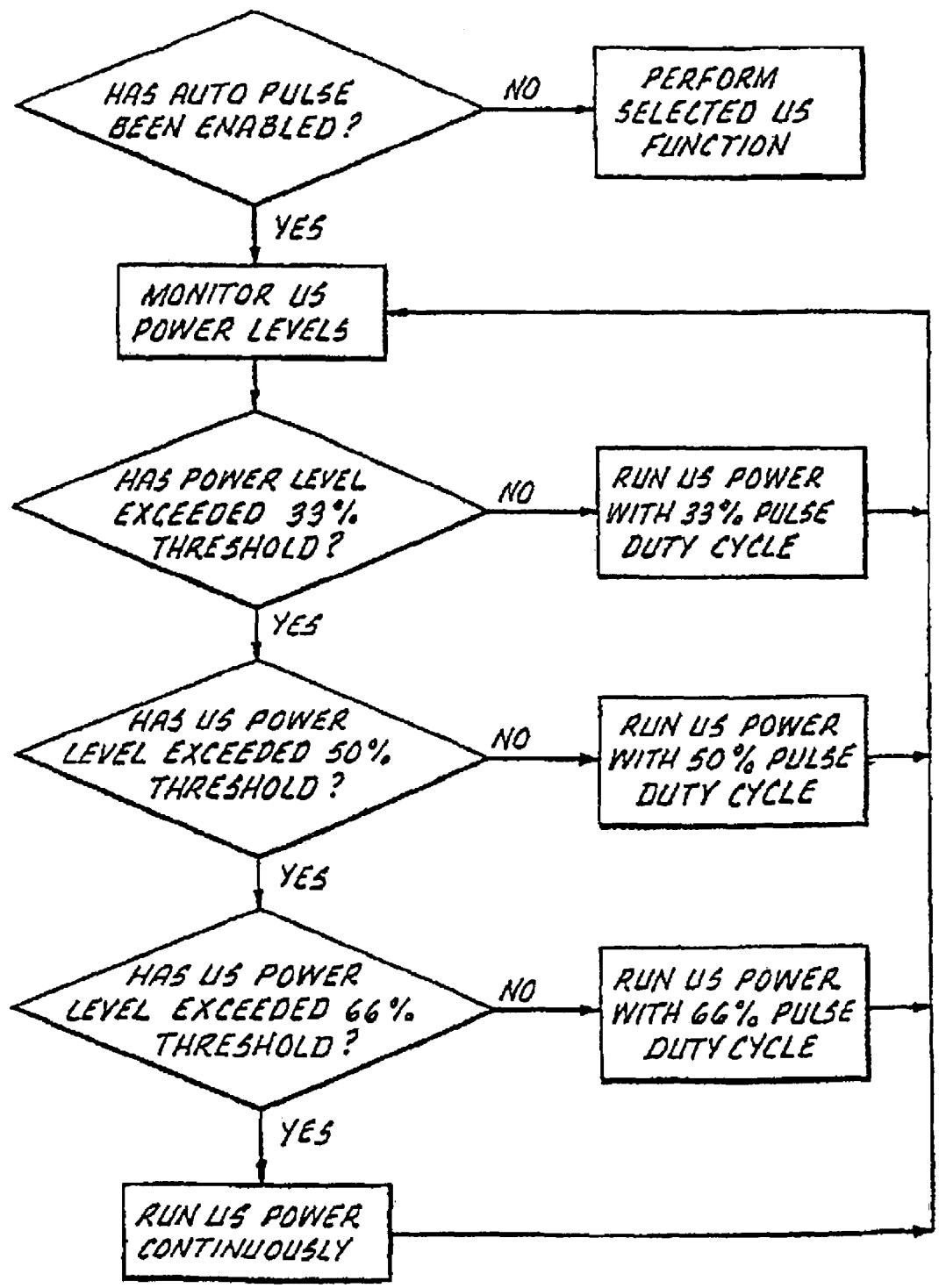
FIG. 5 is a flow chart illustrating the operation of a variable duty cycle pulse function of the phacoemulsification system.

The following sections deal generally with the types of delivery of microburst energy generally employed to effectively carry out the phacoemulsification procedure. With reference to FIG. 5, there is shown a flow diagram depicting basic control of the ultrasonic power source 16 to produce varying pulse duty cycles as a function of selected power levels. Each power pulse may have a duration of less than 20 milliseconds. As shown in FIG. 5, and by way of illustration only, a 33% pulse duty cycle is run until the power level exceeds a preset threshold; in this case, 33%. At that point, the pulse duty cycle is increased to 50% until the ultrasonic power level exceeds a 50% threshold, at which point the pulse duty cycle is increased to 66%. When the ultrasonic power level exceeds 66% threshold, the power source is run continuously, i.e., a 100% duty cycle. Although the percentages of 33, 50 and 66 have been illustrated in FIG. 5, it should be understood that other percentage levels can be selected as well as various duty cycles to define different duty cycle shift points. The pulse duration in this arrangement may be less than 20 milliseconds. This control along with the tracking mechanism herein described enables bursts of energy less than 20 milliseconds in duration.

Figure 13:
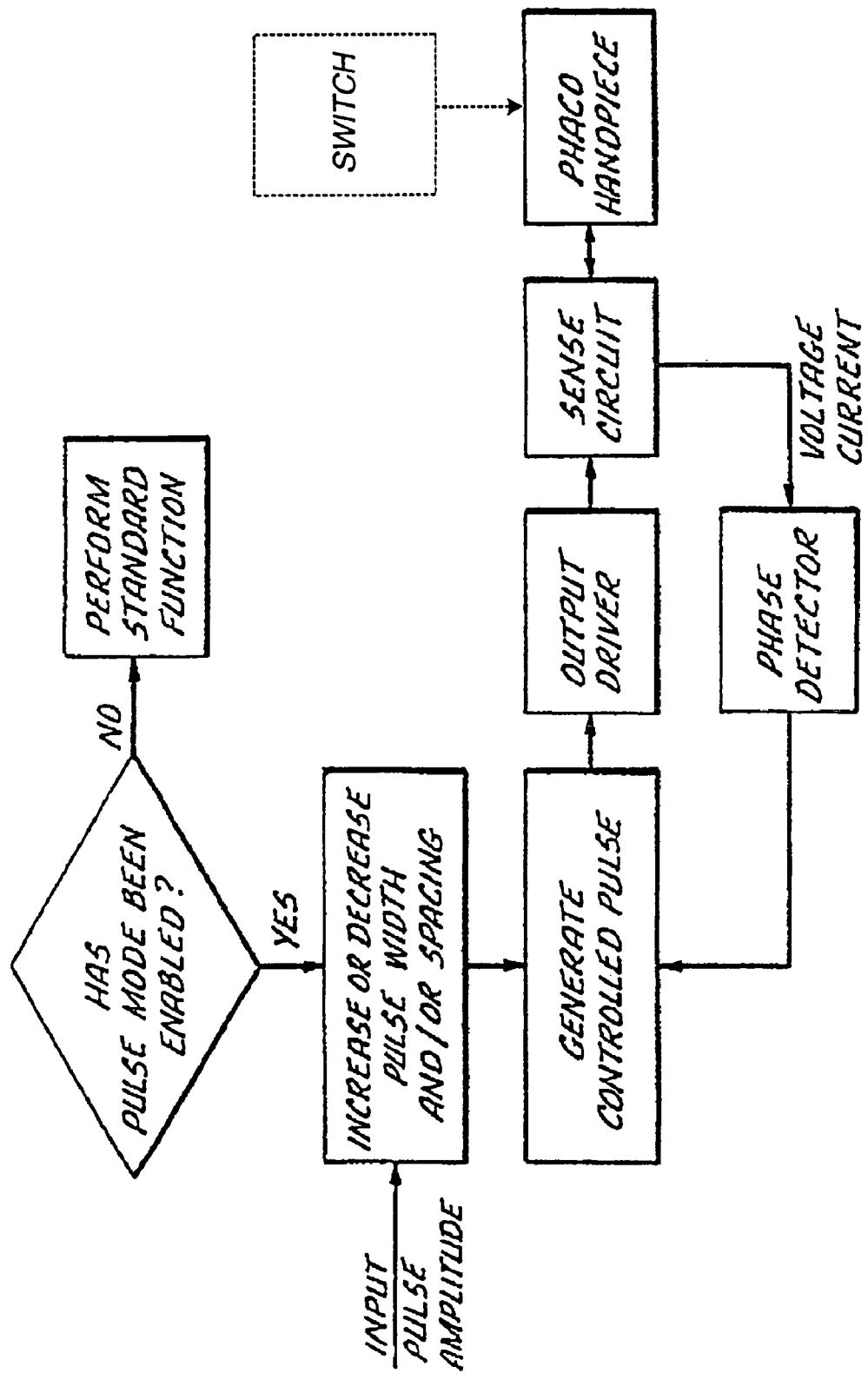
FIG. 13 is a function block control diagram of a pulse control phacoemulsification system.

With reference to FIG. 13, a rapid pulse duration of less than 20 milliseconds is provided with adequate energy to cut the tissue with kinetic or mechanical energy. The ultrasonic energy pulse may then be turned off long enough to significantly decrease the resultant heat level before the next pulse is activated. A surgeon/operator may vary the pulse amplitude in a linear manner via the switch 143 and the control unit 22 in response to the selected pulse amplitude, irrigation and aspiration fluid flow rates, controlling a pulse duty cycle. As hereinabove noted, an off duty duration or cycle is provided to ensure heat dissipation before a subsequent pulse is activated. In this way, increased amplitude will increase tip acceleration and thus heat dissipation level for tissue damaging heat generation. That is, the surgeon/operator can use linear power control to select the correct acceleration necessary to cut through the tissue density while the control unit provides a corresponding variation in pulse width of less than 20 milliseconds and "off time" to prevent tissue de-compensation from heat. The control unit is programmed depending on the phacoemulsification handpiece chosen (total wattage) or the phacoemulsification tip (dimensions, weight). This use of rapid pulsing is similar to how lasers operate with very short duration pulses. Pulses in this configuration may have a repetition rate of between about 25 and 2000 pulses per second.

With reference to FIG. 5, if the handpiece aspiration line 38 is occluded, the vacuum level sensed by the vacuum sensor 24 will increase. The computer 18 has operator-settable limits for controlling which of the irrigation fluid supplies 32, 33 will be connected to the handpiece 30. While two irrigation fluid sources, or containers 32, 33 are shown, any number of containers may be utilized.

As shown in FIG. 6, when the vacuum level by the vacuum sensor 24 reaches a predetermined level, as a result of occlusion of the aspiration handpiece line 38, the computer controls the valve 38 causing the valve to control fluid communication between each of the containers 34, 35 and the handpiece/needle 30.

Depending upon the characteristics of the material occluding the handpiece/needle 30, as hereinabove described and the needs and techniques of the physician, the pressure of irrigation fluid provided the handpiece may be increased or decreased. As occluded material is cleared, the vacuum sensor 24 may register a drop in the vacuum level causing the valve 38 to switch to a container 34, 35, providing pressure at an unoccluded level.

More than one container may be utilized, such as three containers (not shown) with the valve interconnecting to select irrigation fluid from any of the three containers, as hereinabove described in connection with the container system.

In addition to changing phacoemulsification handpiece/needle 30 parameter as a function of vacuum, the occluded or unoccluded state of the handpiece can be determined based on a change in load sensed by a handpiece/needle by way of a change in phase shift or shape of the phase curve. A plot of phase angle as a function of frequency is shown in FIG. 10 for various handpiece 30 loading, a no load (max phase), light load, medium load and heavy load.

Figure 10:
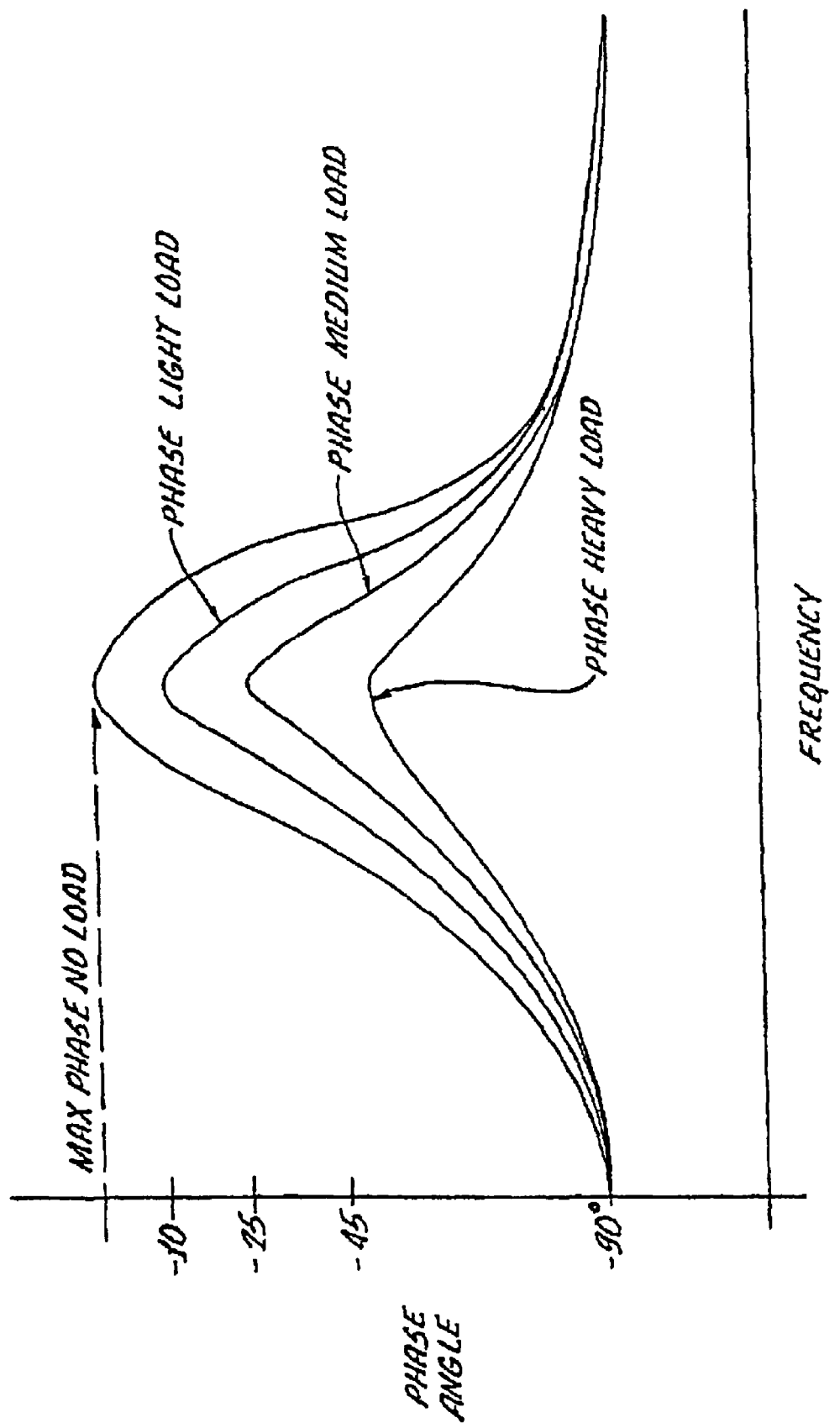
FIG. 10 is a plot of phase relationship as a function of frequency for various handpiece/needle loading.
Figure 11:
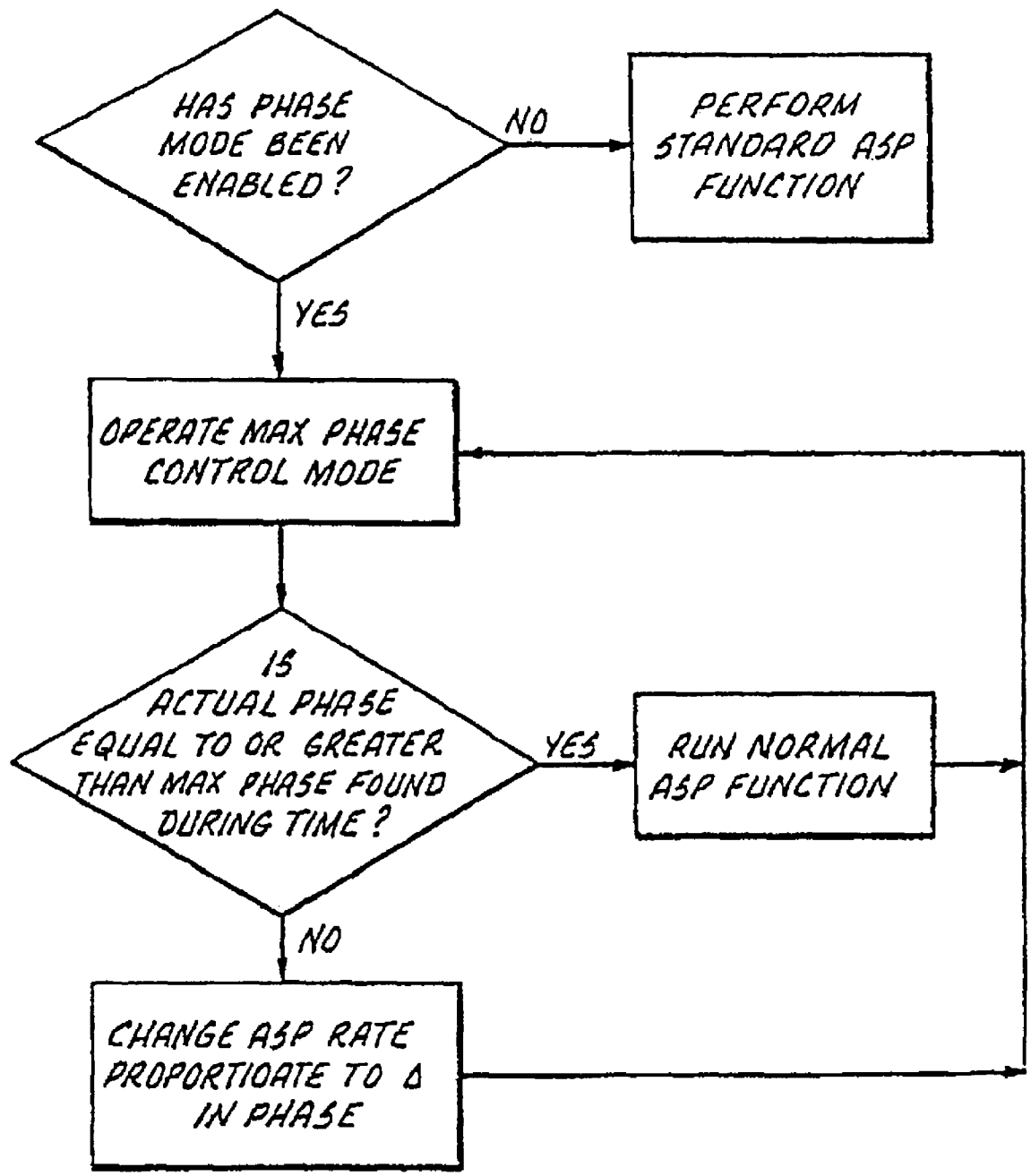
FIG. 11 is a function block diagram of a phase control phacoemulsification system utilizing phase angles to control handpiece/needle parameters with max phase mode operation.
Figure 12:
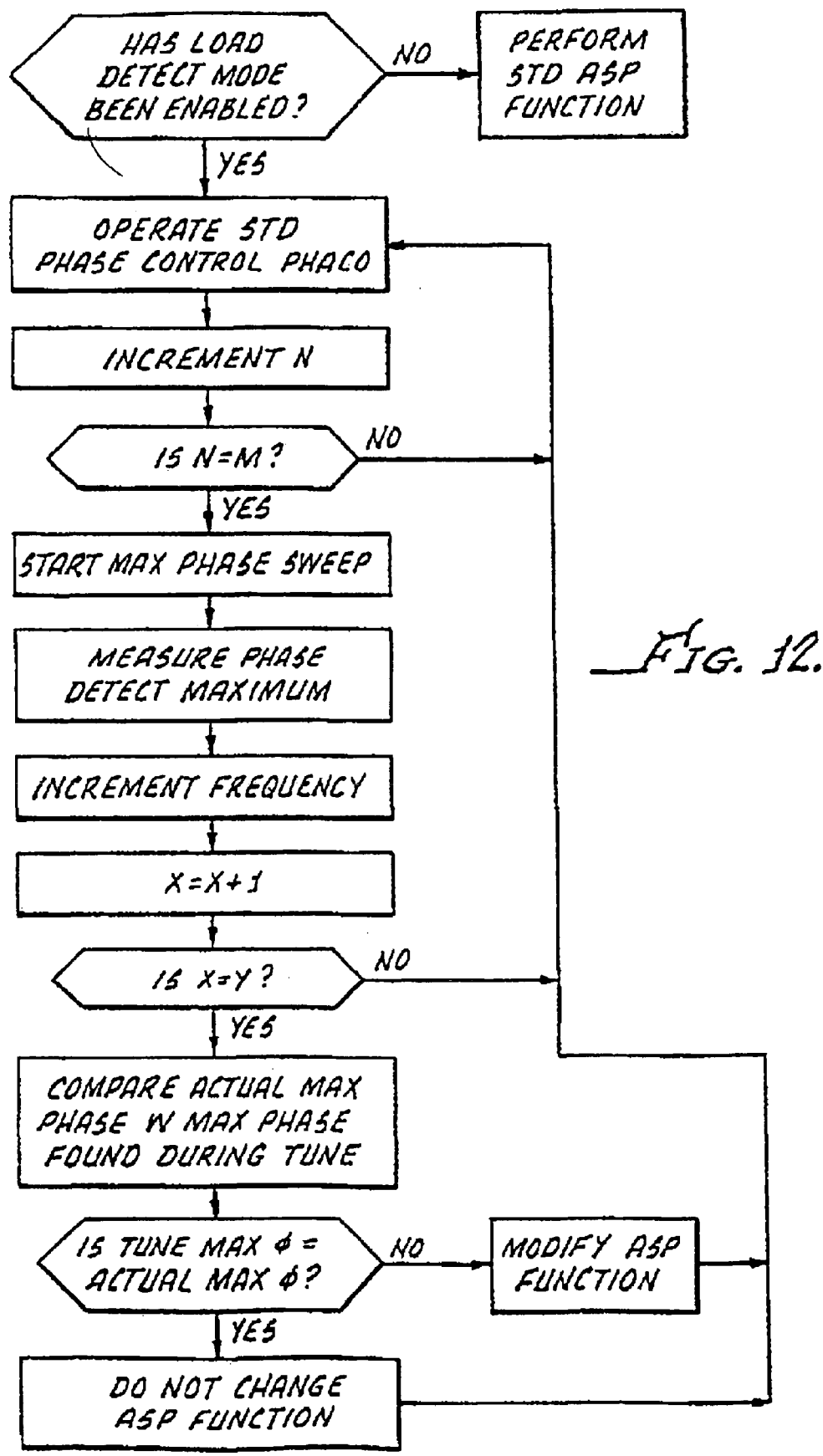
FIG. 12 is a function block control diagram of a phase control phacoemulsification system utilizing phase angles to control handpiece/needle parameters with a load detect method.

With reference to FIG. 11, representing max phase mode operation, the actual phase is determined and compared to the max phase. If the actual phase is equal to, or greater than, the max phase, normal aspiration function is performed. If the actual phase is less than the max phase, the aspiration rate is changed, with the change being proportionate to the change in phase. FIG. 12 represents operation at less than max load in which load (see FIG. 10) detection is incorporated into the operation.

As represented in FIG. 11, representing max phase mode operation, if the handpiece aspiration line 40 is occluded, the phase sensed by phase detector sensor 28 will decrease (see FIG. 10). The computer 18 has operator-settable limits for aspiration rates, vacuum levels and ultrasonic power levels. As illustrated in FIG. 11, when the phase sensed by phase detector 28 reaches a predetermined level as a result of occlusion of the handpiece aspiration line 40, computer 18 instructs pump speed controller 20 to change the speed of the peristaltic pump 14 which, in turn, changes the aspiration rate.

Depending upon the characteristics of the material occluding handpiece/needle 30, the speed of the peristaltic pump 14 can either be increased or decreased. When the occluding material is broken up, the phase detector 28 registers an increase in phase angle, causing computer 18 to change the speed of peristaltic pump 14 to an unoccluded operating speed.

In addition to changing the phacoemulsification parameter of aspiration rate by varying the speed of the peristaltic pump 14, the power level and/or duty cycle of the ultrasonic power source 16 can be varied as a function of the occluded or unoccluded condition of handpiece 30 as hereinabove described.

Microburst Enhanced Operation.

Figure 14:
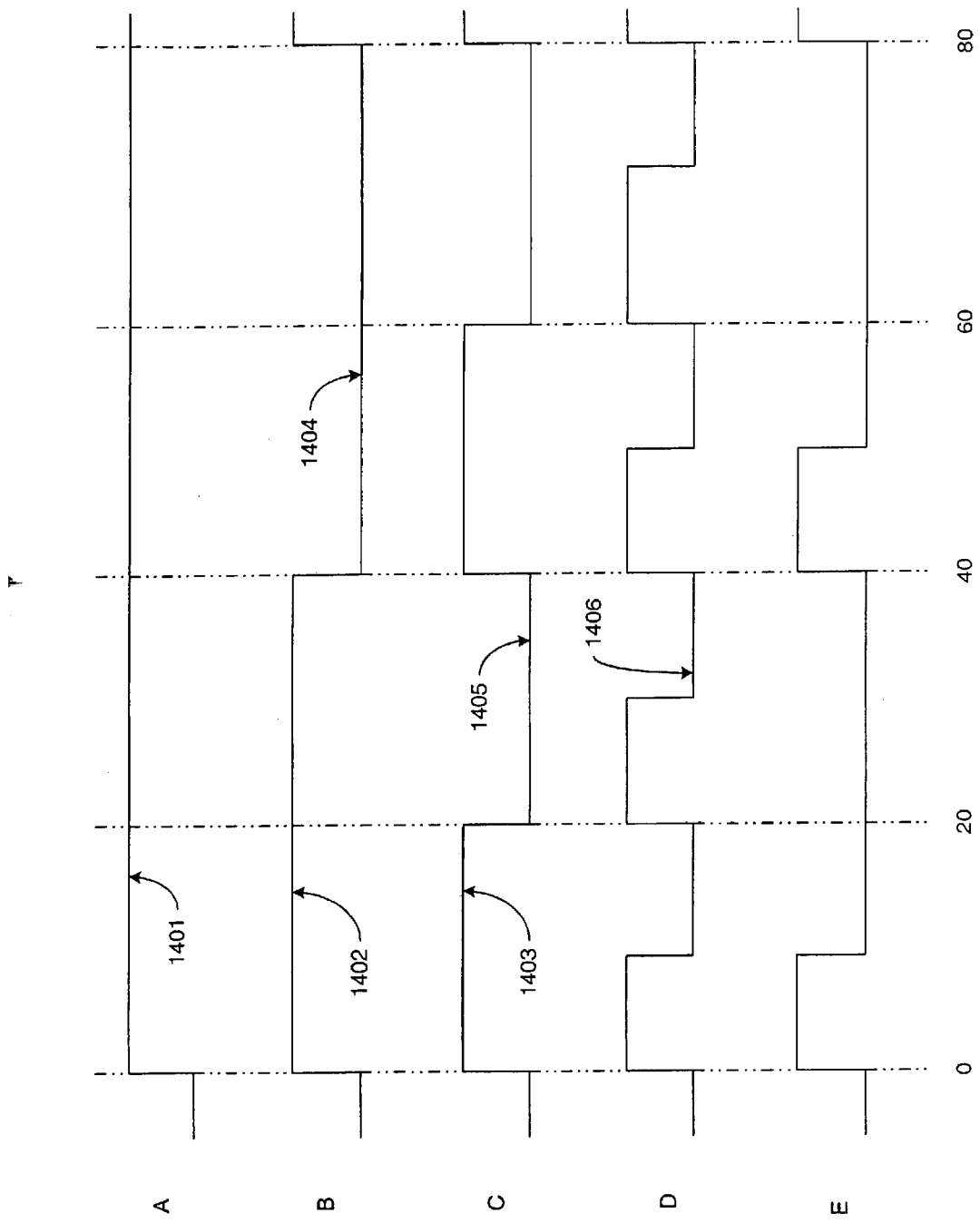
FIG. 14 illustrates different ultrasonic energy pulse characteristics for pulses provided by the power level controller and computer via the handpiece.

From the foregoing, a representation of different pulse characteristics for the microburst operation is presented in FIG. 14. From FIG. 14, operation of pulses may be a constant application of power at a frequency of between about 25 kHz to about 50 kHz as illustrated in Plot A, or once every 80 milliseconds for a duration of 40 milliseconds on and 40 milliseconds off as in Plot B, representing 12.5 pulses per second. Alternately, ultrasonic power delivery may occur once every 40 ms, for 20 ms on and 20 ms off as in Plot C. Plot D shows power applied every 20 ms for 10 ms and turned off for 10 ms. Other non periodic arrangements may be employed, such as shown in Plot E, with application of power for 10 ms periodically every 40 ms, with a resultant 30 ms off time.

These power application intervals represent solid, constant periods when ultrasonic power is being applied to the handpiece and needle at a constant power level for a period of time. Again, while power may appear in the Figures to be applied at a continuous DC type of application, the Figures are intended to indicate actual application of power including a sinusoidal waveform being applied to the piezoelectric crystals at a frequesncy of generally between about 25 kHz and 50 kHz. The application of power is therefore not truly "constant." Application of power during this 150 ms period is defined as a constant application of a 25 kHz to 50 kHz sinusoid. Further, as used herein, the term "long on period," or "pulsed energy on period" represents that period of constant application of power as illustrated in FIG. 14, such as the period 1401 in Plot A, period 1402 in Plot B, and 1403 in Plot C. The term "long on period" represents any application of power greater than approximately 10 milliseconds in the environment shown. In other environments or under different circumstances, such as when used with a different type of handpiece, the "long on period" could be shorter in duration. The term "long off period" as used herein represents that period of rest or de minimis or trivial power application or rest between the "long on periods." Such "long off periods" are exemplified by period 1404 in Plot B, period 1405 in Plot C, and period 1406 in Plot D. As used herein, the term "minimal" power when used in accordance with the short rest period or the long off period means a zero, minimal, small, or relatively trivial amplitude of power applied, but not necessarily the "minimum" amplitude that may be applied by the system. "Long off periods" are also generally greater than approximately 10 milliseconds in the environment shown, and the amplitude of power applied during the long off period may be nonzero, including but not limited to some small, de minimis or trivial amount. In other environments or under different circumstances, such as when used with a different type of handpiece, the "long off period" could also be shorter in duration.

Application of power in the arrangement shown may produce significant amounts of heat to the treated region, and the application of power can cause stable cavitation, which may inhibit the ability to collect pieces that have broken from the phakic lens and are floating in the region.

Figure 15A:
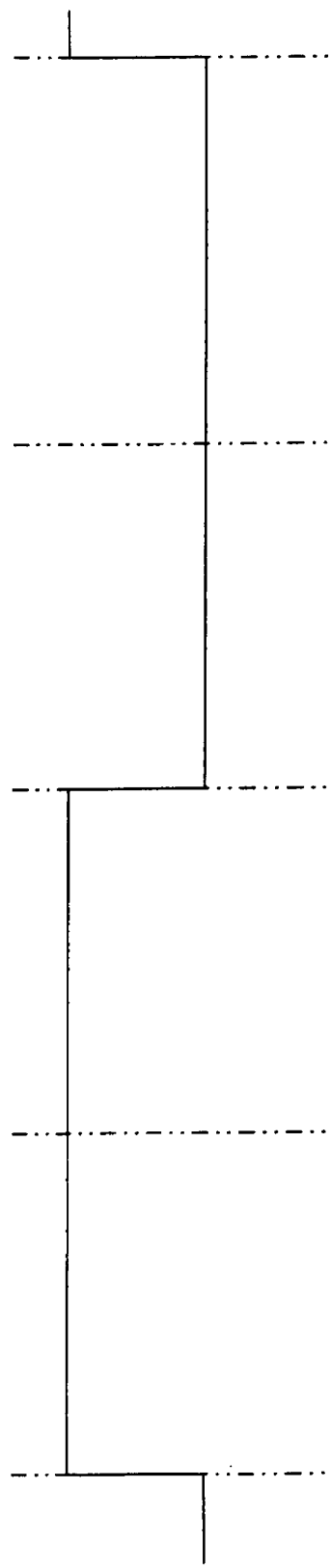
FIG. 15A is a prior art ultrasonic energy waveform generated having a constant long on period and a constant long off period.
Figure 15B:
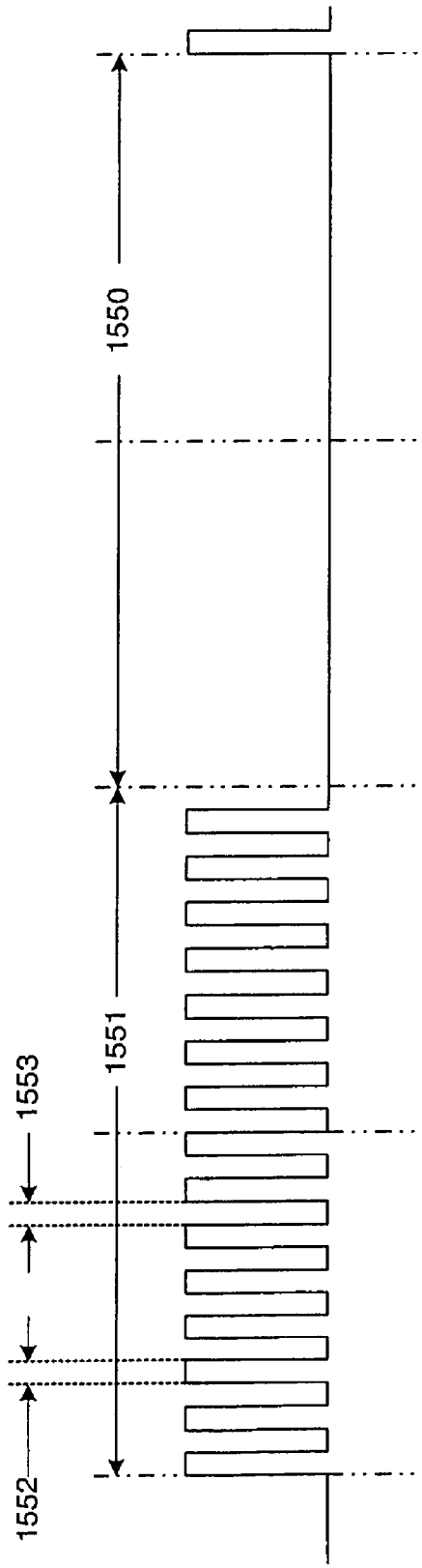
FIG. 15B is an ultrasonic energy waveform according to one aspect of the present invention having a pulsed on period followed by a long off period.

The present invention entails splitting the long on period into a plurality of short on periods partitioned by short off periods. The basic arrangement for the previous implementation and the enhanced microburst implementation is illustrated in FIGS. 15A and 15B. FIG. 15A shows a long on period of 60 ms followed by a long off period of 60 ms according to the long on period/short on period implementation of the prior art. FIG. 15B illustrates a 60 ms "on" period containing 15 ultrasonic energy bursts comprising an ultrasonic energy pulse on for two milliseconds, followed by a two millisecond rest period. The ultrasonic energy pulses are delivered at a substantially constant ultrasonic power level. The period of 15 2 millisecond power bursts is followed by a long off period of 60 ms of no ultrasonic power application similar to the long off period of FIG. 15A.

Application of power in the arrangement shown may therefore include four variables alterable by either the surgeon/operator or automatically by the system at any time, namely the long off period 1550, the long on period 1551, the short on period 1552, and the short off period 1553.

This bursting method lowers the overall power applied to the target region, resulting in application of less heat to the affected region. This bursting method further decreases adverse effects associated with stable cavitation, and may enhance the clinical efficacy of lens or tissue removal using reduced ultrasonic energy.

For purposes of this application, the term "short on burst" represents a subgroup of an "on" period, significantly shorter than the long off period. The term "short rest period" represents the period between the short on pulses in this configuration wherein zero, de minimis, small, or trivial power is applied via the handpiece. The term "short burst" represents a combination of one short on burst followed by one short rest period.

As noted, the "long on period" in the current configuration is generally in the range of 20 ms or more. The "short on burst" is shorter than the "long on period," and may generally be in the range of approximately 8 ms or less for the configuration described. Again, depending on the application, such as when employing a different phacoemulsification handpiece, the "short on burst" may vary. The "short rest period" is typically in the range of approximately 8 ms or less, but may be longer, and need not be identical in time to the "short on burst." Those of ordinary skill in the art will appreciate that different timing may be employed depending on the circumstances while encompassing the inventive characteristics described herein.

For purposes of discussion, it should be noted that the design disclosed herein can be characterized by a series of "long off periods" alternating with a series of "short rest periods." The "short rest periods" further alternate with a series of "short on bursts." Certain additional implementations may be employed. For example, in the past, certain duty cycles have been employed to perform "sculpting" of the lens region, and others for performing "chop" or "quadrant removal." The previous implementations have used a continuous ultrasonic energy application period for sculpting, while "chop" or "quadrant removal" has been employed using a series of shorter continuous ultrasonic application periods, such as in the range of 50 to 200 milliseconds.

Figure 16B:
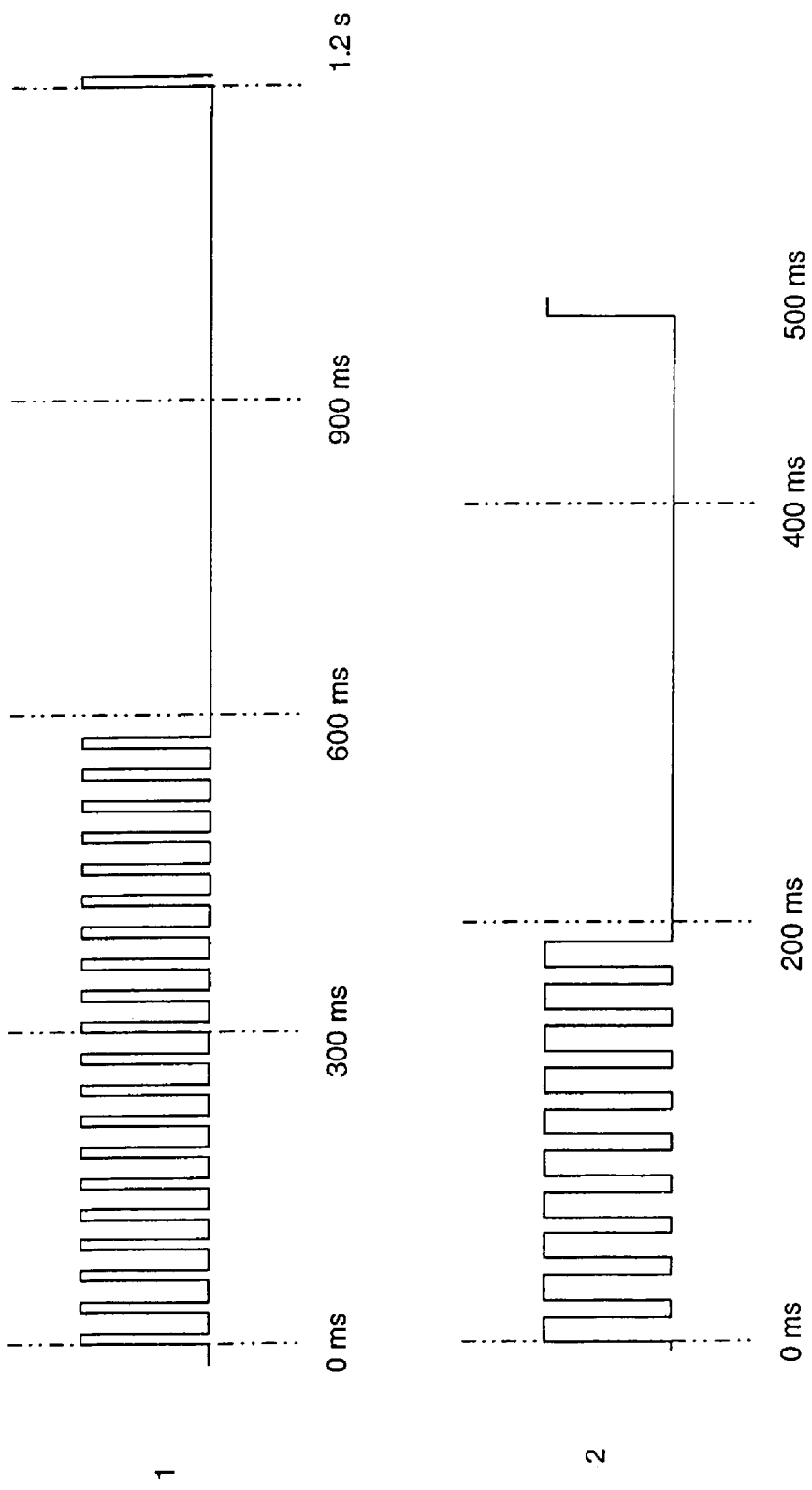
Figure 16C:
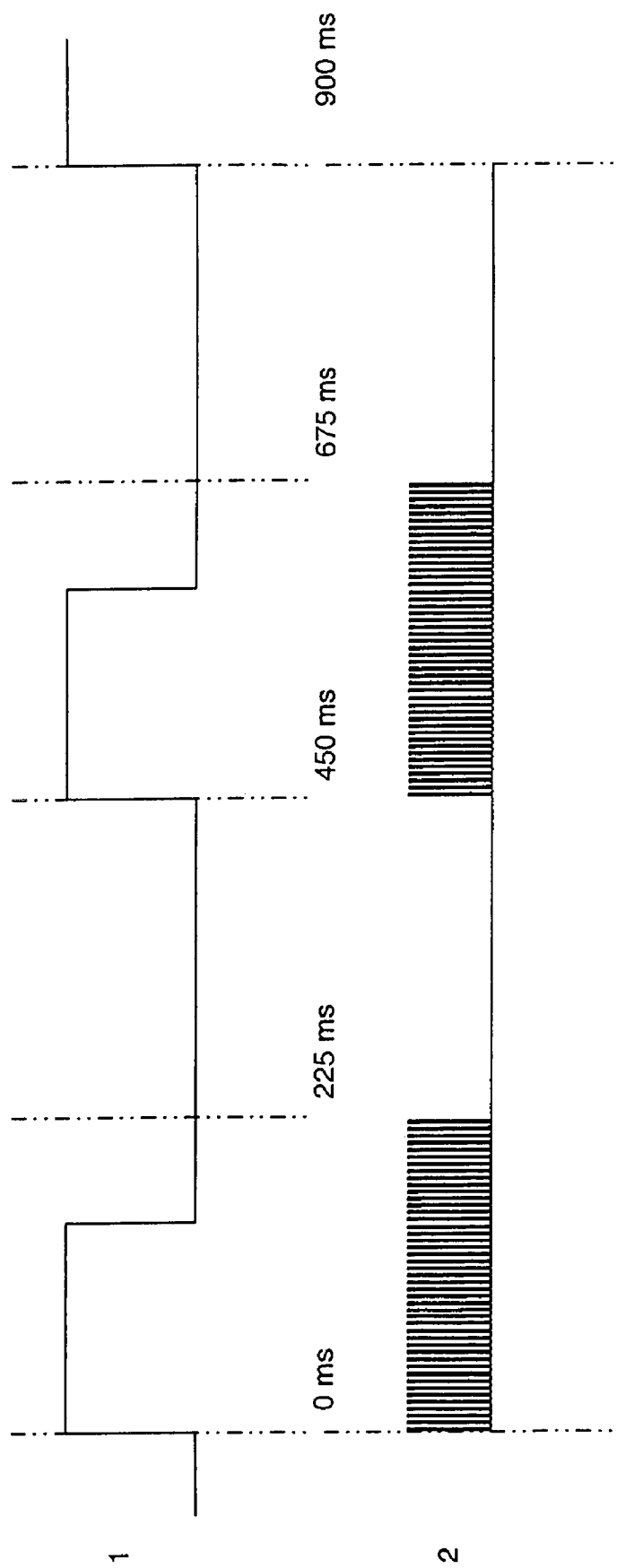

Other time periods may be employed. A few representative aspects are shown in FIGS. 16A, 16B, and 16C, and are not intended to be limiting. As shown, Plot A of FIG. 16A illustrates a solid 1 second application of energy, such as had been previously employed for sculpting procedures of the lens area. This solid one second of ultrasonic energy application represents a 100 percent duty cycle, which can build up a great deal of heat in the affected region fairly rapidly. Plot B of FIG. 16A presents an alternative power application timing sequence that may also be employed during a sculpting procedure, with one 750 ms long on period followed by one 250 ms long off period, a 75 percent duty cycle. This, however, may not be generally clinically acceptable for sculpting due to a perceived lack of smoothness in cutting. Plot C illustrates one aspect of the present invention wherein sculpting is performed using one hundred 7.5 ms short on bursts, each short on burst followed by a 2.5 ms short rest periods, again a 75 percent duty cycle. This burst/rest arrangement, previously not employed in sculpting procedures, sculpts with 30 percent less ultrasonic energy to the affected area and can enable cooling of the region as well as a perceived smooth cut.

Plot 1 of FIG. 16B shows an "burst on" interval of 600 ms, with twenty 10 ms short on bursts each followed by a 20 ms short rest period, followed by a long off period of 600 ms. Plot 2 of FIG. 16B shows a 200 ms "burst on" interval, using 12 ms short on bursts followed by 8 ms short rest periods, where the 200 ms "burst on" interval is followed by a 300 ms long off period. Different "burst on" ranges may be employed, typically in the range of 40 msec to 250 msec during an overall power/energy application period, wherein the remaining time is a long off period. Plot 1 of FIG. 16C shows a previous ultrasonic energy delivery pattern for a quadrant removal procedure using two long pulses of 150 ms in duration over a 1 second period, for a total of 300 milliseconds of ultrasonic energy bursting or a 30 percent duty cycle. Plot 2 of FIG. 16C presents an alternative having a lower duty cycle, with a 5 ms pulse having a short on burst of 1.5 ms followed by a short rest period of 3.5 ms for 225 ms, with a 225 ms long rest period afterward, resulting in, for the configuration shown, a 15 percent duty cycle. Such an implementation can allow for efficient cutting of the ocular quadrant, or quadrant removal, enabling a handpiece vacuum to attract or hold fragments of the lens being removed.

The pulsing of energy described herein may be performed in software, hardware, firmware, or any combination thereof, or using any device or apparatus known to those skilled in the art when programmed according to the present discussion. A sample block diagram of the operation of the invention as may be implemented in software is presented in FIG. 17, which is an extension of the implementation of FIG. 13. From FIG. 17, after evaluating whether pulse mode has been enabled, the system evaluates whether enhanced pulse mode has been enabled. If not, the system proceeds according to FIG. 13.

If enhanced pulse mode has been enabled, the Settings Required are received. Settings Required may include, but are not limited to, overall cycle time, a desired procedure or function to be performed (sculpting, chopping, etc.), desire to provide bursts or long continuous periods of power application, desired "burst on" period, desired "long on period," desired "long off period," desired "short on burst" period, desired "short rest period," and/or other pertinent information. Certain lookup tables may be provided in determining Settings Required, including but not limited to tables associating popular settings with the specific performance parameters for the desired setting. For example, if the desired function is "chop," the system may translate the desired "chop" function selection into a standardized or predetermined set of performance parameters, such as a 150 millisecond "burst on" period, followed by an 350 ms "long off period," where the "burst on" period comprises 2 millisecond "short burst period" followed by a 3 millisecond "short rest period." The system takes the Settings Required and translates them into an Operation Set, or operation timing set, the Operation Set indicating the desired operation of the phacoemulsification handpiece tip when performing ultrasonic energy or power delivery.

Input 1702 represents an optional input device, such as a foot pedal, electronic or software switch, switch available on the phacoemulsification handpiece, or other input device known to those skilled in the art, that allows the surgeon/operator to engage and enable ultrasonic power to be applied according to the operation set. For example, a foot pedal may be supplied that issues an on/off command, such that when depressed power is to be applied according to the operation set, while when not depressed power is not supplied to the phacoemulsification handpiece tip. Different input devices may enable different modes of operation. For example, a multiple position switch may be provided that allows for application of ultrasonic power according to one Operation Set, while moving the switch to another position allows for application of ultrasonic power according to a different Operation Set. Alternately, one position of the switch may allow for power application at one level according to one Operation Set, while another position of the switch may enable a higher ultrasonic power level at the same or a different operational timing set. Operation Set as used herein refers to the timing of pulses and/or energy applications and on/off periods for the application of power as described herein. Switching may also be nonlinear, such as one detent or setting for the switch providing only irrigation to the handpiece, a second detent or setting providing a pump on plus irrigation, and a third detent or setting providing irrigation and aspiration wherein ultrasound is introduced and may be increased by applying further engagement of the switch or foot pedal. In this instance, a foot pedal depressed to the third position or detent will enable the operator or surgeon to apply energy according to a base operational timing set and amplitude, such as a first operational timing set with a first amplitude, while further depression of the foot pedal would allow application of a second operational timing set and/or a second amplitude. If increased amplitude is desired, depressing the foot pedal past the third detent may linearly change the amplitude from a value of 0% of available ultrasonic power or tip stroke length to a value of 100% of ultrasonic power or tip stroke length, or some other value between 0% and 100%. In the present design, amplitudes during energy application periods typically range from about 0 watts to 35 watts at 100% power.

As may be appreciated, virtually any operation set and operation timing set may be employed while within the course and scope of this invention. In particular, the system enables operation in multiple configurations or operational timing sets, each typically accessible to the user via the computer. For example, the user may perform a chop operation using one operational timing set, a sculpt operation using another operational timing set, and when encountering particular special conditions employing yet another operational timing set. These configurations may operate dynamically, or "on the fly."

The system typically has a frame rate, which may be any period of time less than the smallest allowable power on or power off period for the device. A counter counts the number of pulses, and if the Operation Set dictates that ultrasonic power is to be delivered at a certain frame number, an indication in the form of an electronic signal is delivered to the handpiece tip at that frame time. Other implementations beyond that shown in FIG. 17 may be employed while still within the scope of the present invention.

Figure 18A:
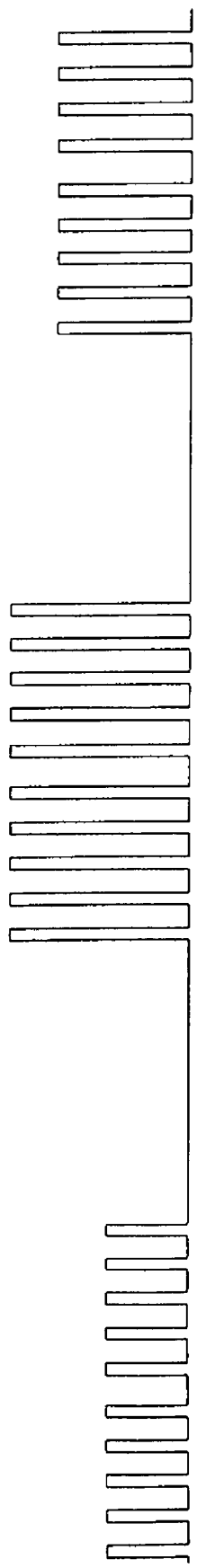
FIG. 18 illustrates an exemplary set of waveforms provided in the presence of an occlusion or other sensed change in flow, pressure, or vacuum conditions.
Figure 18B:
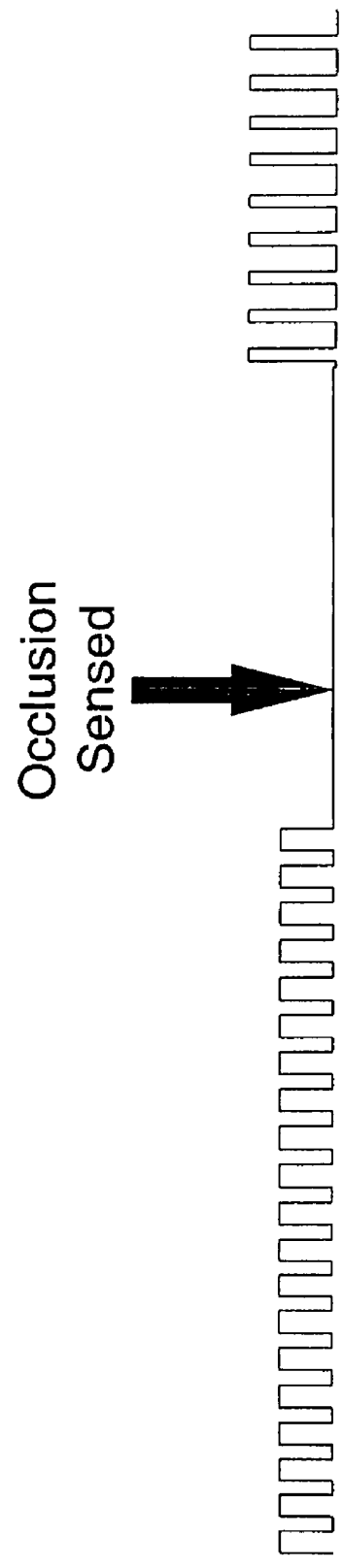

FIG. 18A illustrates the automatic or user controlled altering of the amplitude, with three different amplitude levels having the same timing. Alternate timing may be made available in addition to the different amplitudes. Additionally, the system may operate to address receipt or encounter of an occlusion as sensed by a sensor, typically located in the system. As in FIGS. 3 and 4, the handpiece or system may employ a sensor to sense a change in flow or vacuum, i.e. pressure, conditions. A change in flow or vacuum/pressure conditions sensed by the sensor indicates the presence of an occlusion, and upon sensing the presence of an occlusion, the handpiece or system may feed back an occlusion indication to the computer 18. An occlusion indication may cause the computer 18 to automatically alter the Operation Set to an occlusion related Operation Set such as that illustrated in FIG. 18B.

Figure 19:
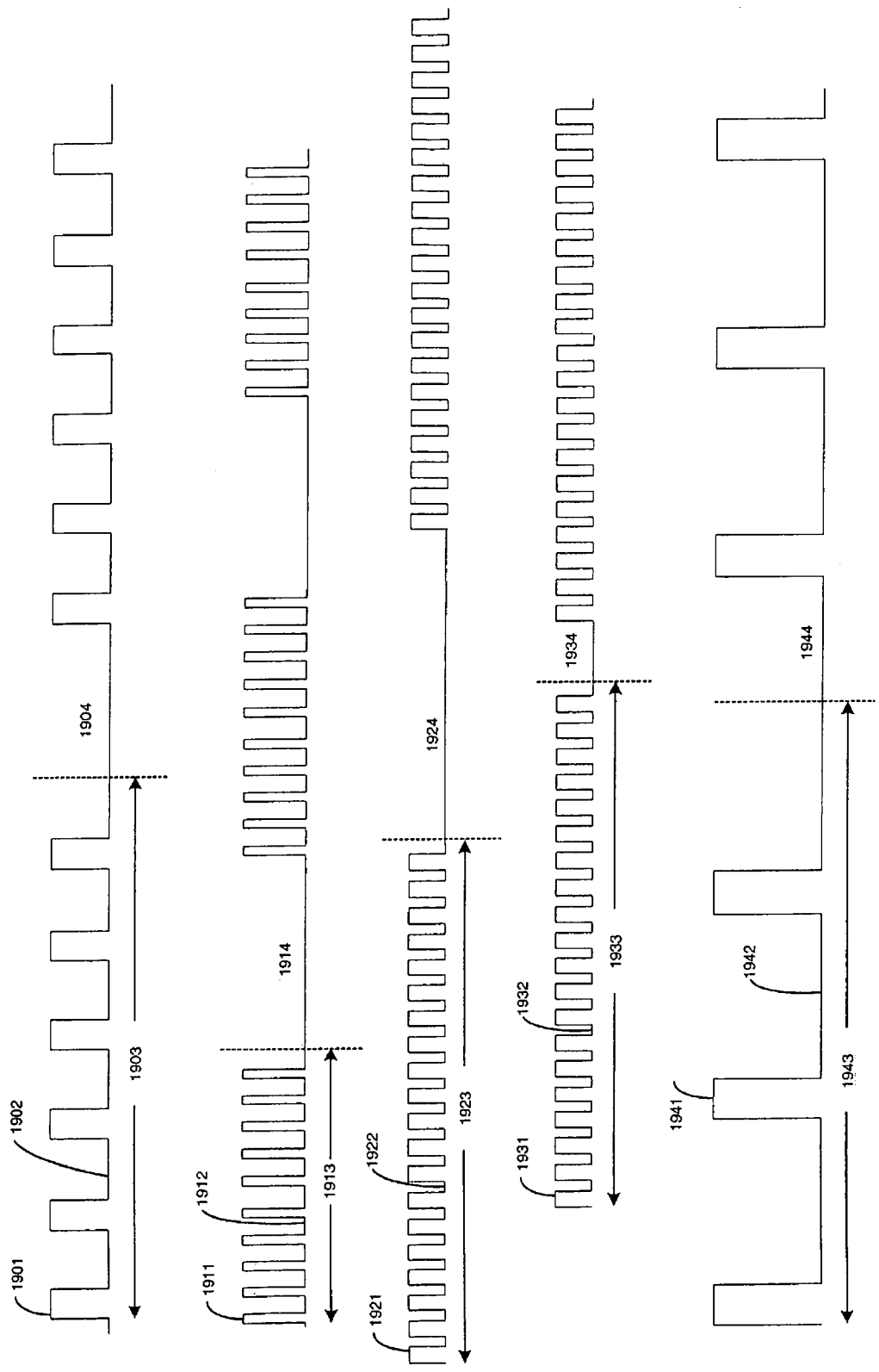
FIG. 19 illustrates further alternate examples of timing arrangements in accordance with the present design.

Further alternate timing and amplitude arrangements are presented in FIG. 19, again intended as exemplary and not intended to be limiting. Short on bursts 1901, 1911, 1921, 1931, and 1941 are followed by short rest periods 1902, 1912, 1922, 1932, and 1942, with a burst on or on periods, or intervals, 1903, 1913, 1923, 1933, and 1943, with long off periods 1904, 1914, 1924, 1934, and 1944. It should be appreciated that certain energy spikes or transmissions may occur during the long off period or periods, but the overall effect of the energy delivered is the plurality of short on bursts alternating with short rest periods, with long off periods including minimal energy transmission. The present design therefore contemplates long off periods wherein zero, small, de minimis or trivial amounts of energy are transmitted, or long off periods wherein spurious or relatively ineffective transmissions occur.

It will be appreciated to those of skill in the art that the present design may be applied to other systems that perform tissue extraction, such as other surgical procedures used to remove hard nodules, and is not restricted to ocular or phacoemulsificaiton procedures. In particular, it will be appreciated that any type of hard tissue removal, sculpting, or reshaping may be addressed by the application of ultrasonic power in the enhanced manner described herein.

Although there has been hereinabove described a method and apparatus for controlling the ultrasonic power transmitted from a phacoemulsification handpiece utilizing, inter alia, the voltage current phase relationship of the piezoelectric phacoemulsification handpiece and delivering ultrasonic power using relatively short pulses comprising multiple brief power bursts and brief rest periods, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for delivering energy during a surgical procedure, comprising:
applying ultrasonic energy during at least one pulsed energy on period, wherein applying energy during the pulsed energy on period comprises:
applying ultrasonic energy during a series of short burst periods, said short burst periods interspersed by short rest periods wherein minimal energy is applied; and
refraining from delivering ultrasonic energy during a long off period, the long off period comprising a relatively long period when minimal energy is applied, wherein one long off period follows each pulsed energy on period;
wherein said short burst periods and said short rest periods are relatively brief in duration as compared with said long off period.

2. The method of claim 1, wherein the short burst period is at most approximately ten milliseconds and the short rest period is at most approximately twenty five milliseconds.

3. The method of claim 2, wherein the long off period is at least about 20 milliseconds.

4. The method of claim 1, wherein the energy applied during the pulsed energy on period and series of short burst periods is of approximately the same magnitude.

5. The method of claim 1, wherein multiple pulsed energy on periods are interspersed with multiple long off periods.

6. The method of claim 1, further comprising engaging the method at a first desired time when energy application is desired and disengaging the method at a second desired time when energy application is not desired.

7. The method of claim 6, wherein said engaging and disengaging is accomplished by a switch.

8. The method of claim 1, further comprising applying ultrasonic energy during at least one additional pulsed energy on period, wherein applying ultrasonic energy during the additional pulsed energy on period comprises:

applying ultrasonic energy during an additional series of short burst periods, said additional short burst periods interspersed by additional short rest periods wherein minimal energy is applied; and refraining from delivering ultrasonic energy during an additional long off period, the additional long off period comprising an additional relatively long period when minimal energy is applied, wherein one additional long off period follows each additional pulsed energy on period;

wherein said additional short burst periods and said additional short rest periods are relatively brief in duration as compared with said additional long off period.

9. A method of delivering ultrasonic energy during a tissue removal procedure, comprising:
  delivering pulses of ultrasonic energy during an on period, energy pulse delivery comprising:
    delivering at least one relatively short burst of energy; and
    pausing for at least one relatively short period; and
    pausing for a relatively long off period after said on period and prior to commencing any subsequent on period, wherein pausing for each relatively, short period and for the relatively long off period comprises applying minimal energy therein;
  wherein each relatively long off period automatically occurs after each on period and occurs in the absence of external energy level reduction activities.

10. The method of claim 9, wherein said relatively long off period is longer in duration than the relatively short off period and the relatively short burst of energy.

11. The method of claim 10, wherein the relatively short burst period is at most approximately ten milliseconds and the relatively short off period is at most approximately twenty five milliseconds.

12. The method of claim 11, wherein the relatively long off period is at least about 20 milliseconds.

13. The method of claim 9, wherein the energy applied during each relatively short burst period is approximately the same magnitude.

14. The method of claim 9, wherein multiple on periods are employed interspersed with multiple relatively long off periods.

15. The method of claim 9, further comprising engaging the method at a first desired time when energy application is desired and disengaging the method at a second desired time when energy application is not desired.

16. The method of claim 15, wherein said engaging and disengaging is accomplished by means of a switch.

17. The method of claim 9, wherein pulse delivery further comprises an ability to dynamically alter power application parameters, wherein power application parameters altered comprise performance of at least one from a group comprising the on period, the relatively short burst of energy, the relatively short pause period, and the relatively long off period.

18. The method of claim 17, wherein one of the power application parameters altered comprises amplitude of energy applied during the relatively short burst of energy.

19. A method for providing ultrasonic energy to an ocular region during a phacoemulsification procedure, the method comprising:
  applying ultrasonic energy to the ocular region during at least one pulsed energy on period followed by a long off period, wherein applying ultrasonic energy to the ocular region during the pulsed energy on period comprises:
    applying ultrasonic energy to the ocular region during the phacoemulsification procedure in a series of short burst periods having duration of at most approximately ten milliseconds, said short burst periods interspersed by short rest periods, said short rest periods having minimal power application for at most approximately twenty five milliseconds.

20. The method of claim 19, wherein the energy applied during the pulsed energy on period and series of short burst periods is of approximately the same magnitude.

21. The method of claim 19, further comprising engaging the method at a first desired time when energy application is desired and disengaging the method at a second desired time when energy application is not desired.

22. The method of claim 21, wherein said engaging and disengaging is accomplished by means of a switch.

23. A method of delivering ultrasonic energy during ocular surgery, comprising:
  delivering pulses of energy during an on period, energy pulse delivery comprising:
    delivering at least one relatively short burst of energy; and
    pausing for at least one relatively short period; and
    pausing for a relatively long off period after said on period and prior to commencing any subsequent on period, wherein pausing for each relatively short period and for the relatively long off period comprises applying minimal energy therein;
  wherein the relatively long off period comprises a relatively long period when minimal energy is applied, wherein one long off period follows each pulsed energy on period.

24. The method of claim 23, wherein the short burst is at most approximately ten milliseconds and the short period is at most approximately twenty five milliseconds.

25. The method of claim 24, wherein the long off period is at least about 20 milliseconds.

26. The method of claim 23, wherein the energy applied during the on period and the short burst is of approximately the same magnitude.

27. The method of claim 23, wherein multiple on periods are interspersed with multiple long off periods.

28. The method of claim 23, further comprising engaging the method at a first desired time when energy application is desired and disengaging the method at a second desired time when energy application is not desired.

29. The method of claim 28, wherein said engaging and disengaging is accomplished by means of a switch.

30. The method of claim 28, further comprising applying ultrasonic energy during at least one additional pulsed energy on period, wherein applying ultrasonic energy during the additional pulsed energy on period comprises:
  applying ultrasonic energy during an additional series of short burst periods, said additional short burst periods interspersed by additional short rest periods wherein minimal energy is applied; and
  refraining from delivering ultrasonic energy during an additional long off period, the additional long off period comprising an additional relatively long period when minimal energy is applied, wherein one additional long off period follows each additional pulsed energy on period;
  wherein said additional short burst periods and said additional short rest periods are relatively brief in duration as compared with said additional long off period.

* * * * *